(12) United States Patent
Kinz-Thompson et al.

(10) Patent No.: US 9,759,842 B2
(45) Date of Patent: Sep. 12, 2017

(54) FUNCTIONALIZED SURFACES AND METHODS RELATED THERETO

(71) Applicant: The Trustees of Columbia University in the City of New York, New York, NY (US)

(72) Inventors: Colin Kinz-Thompson, New York, NY (US); Ruben L. Gonzalez, Jr., New York, NY (US); James C. Hone, New York, NY (US); Matteo Palma, New York, NY (US); Alexander Alexeevich Godarenko, Springfield, VA (US); Daniel Alexandre Chenet, New York, NY (US); Samuel J. Wind, White Plains, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/444,793

(22) Filed: Jul. 28, 2014

(65) Prior Publication Data

US 2015/0023840 A1    Jan. 22, 2015

Related U.S. Application Data

(63) Continuation-in-part of application No. 13/655,947, filed on Oct. 19, 2012, now abandoned.
(Continued)

(51) Int. Cl.
*G01N 27/00* (2006.01)
*G02B 1/12* (2006.01)
(Continued)

(52) U.S. Cl.
CPC ......... *G02B 1/12* (2013.01); *G01N 33/54373* (2013.01); *G01N 33/54393* (2013.01); *G02B 6/107* (2013.01)

(58) Field of Classification Search
CPC ......... G01N 21/7743; G01N 33/54373; G01N 33/54393; G02B 1/118; G02B 6/107;
(Continued)

(56) References Cited

U.S. PATENT DOCUMENTS 5,973,316 A * 10/1999 Ebbesen et al. .............. 250/216
2007/0077564 A1 * 4/2007 Roitman et al. ................ 435/6
(Continued)

OTHER PUBLICATIONS

U.S. Appl. No. 13/655,947, Oct. 20, 2014, Notice of Abandonment.
(Continued)

*Primary Examiner* — Dennis M White
(74) *Attorney, Agent, or Firm* — Baker Botts L.L.P.

(57) ABSTRACT

The disclosed subject matter provides a nanoaperture having a bottom surface and a side wall comprising gold. A surface of the side wall is passivated with a first functional molecule comprising polyethylene glycol. The bottom surface of the nanoaperture can be functionalized with at least one second molecule comprising polyethylene glycol, for example, a silane-PEG molecule. The second molecule can further include a moiety, such as biotin, which is capable of binding a target biomolecule, which in turn can bind to a biomolecule of interest for single molecule fluorescence imaging analysis. Fabrication techniques of the nanoaperture are also provided.

34 Claims, 22 Drawing Sheets

Related U.S. Application Data

(60) Provisional application No. 61/554,305, filed on Nov. 1, 2011, provisional application No. 61/858,843, filed on Jul. 26, 2013.

(51) Int. Cl.
*G02B 6/10* (2006.01)
*G01N 33/543* (2006.01)

(58) Field of Classification Search
CPC ... G02B 1/12; B01L 2300/0896; B01L 9/527; B01L 2300/0636
See application file for complete search history.

(56) References Cited

U.S. PATENT DOCUMENTS

| | | |
|---|---|---|
| 2008/0032301 A1 | 2/2008 | Rank et al. |
| 2010/0065726 A1 | 3/2010 | Zhong et al. |
| 2010/0118390 A1 | 5/2010 | Blair et al. |
| 2010/0256016 A1 | 10/2010 | Blair et al. |
| 2011/0117637 A1 | 5/2011 | Gray et al. |
| 2011/0222179 A1 | 9/2011 | Monadgemi |
| 2011/0257040 A1* | 10/2011 | Turner et al. ............ 506/16 |
| 2013/0294972 A1 | 11/2013 | Kinz-Thompson et al. |

OTHER PUBLICATIONS

U.S. Appl. No. 13/655,947, Apr. 4, 2014, Non-Final Office Action.

Eid, et al., "Real-Time DNA Sequencing from Single Polymerase Molecules", *Science*, 323(5910):133-138 (2008).

Foquet, et al., "Improved Fabrication of Zero-Mode Waveguides for Single-Molecule Detection", *Journal of Applied Physics*, 103(3):034301 (2008).

Levene, et al., "Zero-Mode Waveguides for Single-Mode Analysis at High Concentrations", *Science*, 299(5607):682-686 (2003).

\* cited by examiner

+ Streptavidin

- Streptavidin

FUNCTIONALIZED SURFACES AND METHODS RELATED THERETO

CROSS REFERENCES TO RELATED APPLICATIONS

This application is a continuation-in-part of U.S. application Ser. No. 13/655,947, filed Oct. 19, 2012, that claims priority to U.S. Provisional Application No. 61/554,305, filed Nov. 1, 2011. This application further claims priority to U.S. Provisional Application No. 61/858,843, filed Jul. 26, 2013. Each of the patent applications listed in this paragraph are incorporated by reference herein in their entireties, and priority to each of which is claimed.

STATEMENT REGARDING FEDERALLY FUNDED RESEARCH

This invention was made with government support under Grant No. RSG-09-053-01-G, awarded by the American Cancer Society. The government has certain rights in this invention.

BACKGROUND

Single-molecule analytical methods can provide insight into biomolecular dynamics, including by extracting characteristics of molecular interactions in complex mixtures where such information could otherwise be lost in ensemble averaging.

The optical confinement generated by it nanoapertures fabricated on a silica substrate can be used to perform single-molecule fluorescence measurements at physiologically relevant background concentrations of fluorophore-labeled biomolecules. For example, zero-mode waveguides (ZMWs), which are sub-wavelength nanoapertures generated in a metal film, can allow observation of single-molecule phenomena. When light is shone through a zero-mode waveguide, photons having wavelengths greater than a threshold value can be prevented from propagating through the waveguide. The remaining evanescent waves can exponentially decay at the glass/water interface of the ZMWs, leading to a very small detection volume near the interface, e.g., on the scale of zeptoliters. Thus, ZMWs can provide improved signal-to-background ratios (SBRs) of single-molecule fluorescence, permitting single fluorophore-labeled biomolecules to be observed in imaging buffers containing physiologically relevant, micromolar concentrations of fluorophore-labeled ligands.

However, such SBR gains of the nanoapertures can be limited to certain concentrations, for example, with fluorophore-labeled biomolecules such as nucleic acids, at concentrations of up to 1 micromolar. Above this concentration of fluorophore-labeled nucleic acids, and at even lower concentrations of fluorophore-labeled proteins, non-specific binding of the fluorophore-labeled biomolecules to the surfaces of the nanoaperture can undermine the SBR gains.

Accordingly, there is a need for nanoapertures with reduced non-specific adsorption of biomolecules.

SUMMARY

The disclosed subject matter provides nanoapertures, such as zero-mode waveguides (ZMWs), and techniques for uses thereof. The present disclosure further provides nanoaperture arrays and methods of fabrication thereof.

In certain embodiments, an example ZMW includes a substrate and a sub-wavelength nanoaperture structure on the substrate. The nanoaperture includes a bottom surface and, can include a side wall formed of gold. A surface of the side wall can be passivated with a layer of a first functional molecule having polyethylene glycol. In certain embodiments, the layer can be a self-assembled monolayer (SAM).

In certain embodiments, the first functional molecule can have a thiol end group, and can be coupled with the surface of the side wall surface of the nanoaperture with a S—Au bond. The first functional molecule can further include polyalkylene disposed between the polyethylene glycol and the thiol end group.

In certain embodiments, the bottom surface of the ZMW nanoaperture can be functionalized with at least one second functional molecule including polyethylene glycol. For example, the second functional molecule can be attached to the bottom surface via a Si—O—Si linkage. The second functional molecule can further include a moiety capable of binding with a target biomolecule. The moiety can be a biotin moiety, and the target biomolecule can be streptavidin. In certain embodiments, the second functional molecule can include a mixture of (1) a molecule having a moiety capable of binding with a target biomolecule, and (2) a molecule having no moiety capable of binding with the target biomolecule.

The disclosed subject matter also provides methods for fabricating ZMWs. In certain embodiments, a ZMW nanoaperture including a bottom surface and a gold side wall can be formed on a substrate, and a surface of the side wall can be passivated with a first functional molecule including polyethylene glycol. The first functional molecule can include a thiol end group.

In certain embodiments, the method further includes functionalizing the bottom surface of the ZMW with at least one second functional molecule including polyethylene glycol. The second functional molecule can include a silane end group. The second molecule can also include a mixture of silane-PEG and silane-PEG-moiety, where the moiety is capable of binding with a target biomolecule. The moiety can be a biotin moiety, and in such case, the target biomolecule can be streptavidin.

In certain embodiments, a nanoaperture array includes a substrate and two or more nanoapertures on the substrate. The nanoapertures each include a bottom surface and can include a side wall formed of gold. A surface of the side wall can be passivated with a layer of a first functional molecule including polyethylene glycol.

In certain embodiments, the first functional molecule on the side walls of the two or more nanoapertures can have a thiol end group, and can be coupled with the surface of the side wall surface of the nanoaperture with a S—Au bond. The first functional molecule can further include polyalkylene disposed between the polyethylene glycol and the thiol end group.

In certain embodiments, the bottom surface of the two or more nanoapertures of the nanoaperture array can be functionalized with at least one second functional molecule including polyethylene glycol. The second functional molecule can further include a moiety capable of binding with a target biomolecule. The moiety can be a biotin moiety, and the target biomolecule can be streptavidin. In certain embodiments, the second functional molecule can include a mixture of (1) a molecule having a moiety capable of binding with a target biomolecule, and (2) a molecule having no moiety capable of binding with the target biomolecule.

The disclosed subject matter also provides microfluidic devices. In certain embodiments, the microfluidic device includes one or more nanoaperture arrays, a support material, one or more inlet ports coupled to the one or more nanoaperture arrays and one or more outlet ports coupled to the one or more nanoaperture arrays.

DETAILED DESCRIPTION

The disclosed subject matter provides nanoapertures with a modified surface adapted for fluorescence imaging of biomolecules, as well as the fabrication of the nanoapertures and uses thereof. The disclosed subject matter further provides nanoaperture arrays and methods for the fabrication of such nanoaperture arrays.

In one aspect, the presently disclosed subject matter provides nanoapertures on a substrate that are bounded by at least one side wall. As used herein "nanoapertures" refer to openings through a metal film configured to allow wavelengths of light to be transmitted through the metal film. Nanoapertures can include zero-mode waveguides (ZMWs), which refer to nanoapertures and nano-wells of sub-wavelengths of light dimensions. In certain embodiments, sub-wavelengths of light can include predetermined wavelengths of light ranging from 10 to 2000 nanometers (nm). For example, and not by way of limitation, sub-wavelengths of light can refer to a specific distance, such as 436 nm, or may also refer to narrow bands of wavelengths, such as 370-475 nm. In certain embodiments, the nanoapertures disclosed herein can include nanoapertures that allow interaction of incident light with the plasmons of the metal film, which can, in some cases, result in extraordinary transmission of light through the nanoaperture.

In certain embodiments, a "ZMW," as disclosed herein, can refer to a nanoaperture of sub-wavelengths of light that can confine incident light at the about 0 nm to the about 50 nm bottom region of the nanoaperture.

Figure 1:
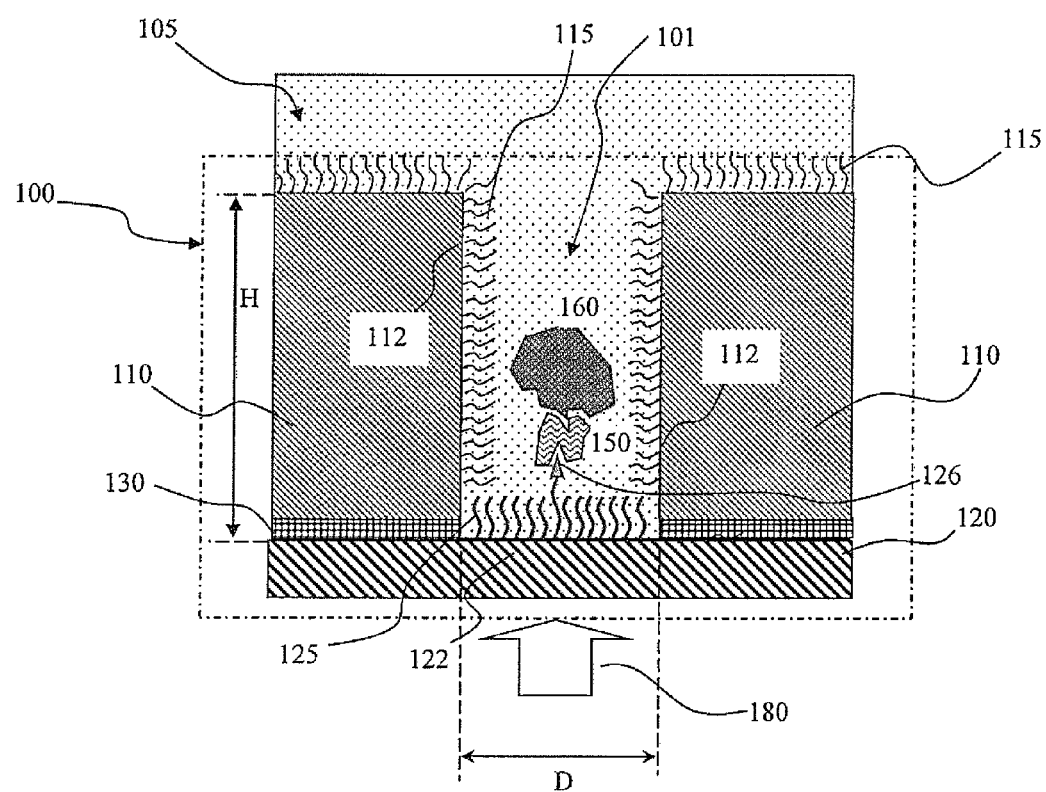
FIG. 1 is a schematic cross-sectional view of a nanoaperture according to some embodiments of the disclosed subject matter.

For purposes of illustration and not limitation, FIG. 1 is a schematic representation of a structure including a nanoaperture according to one embodiment of the disclosed subject matter. The structure can include a substrate 120 and a nanoaperture 101 on the substrate 120. In certain embodiments, the substrate can include a transparent material. For example, and not by way of limitation, the transparent material can be a plastic, glass, silicon wafer or silica.

In certain embodiments, the nanoaperture 101 is bounded by at least one side wall 110 having a surface of 112. The side wall can be made from a noble metal such as gold, e.g., gold cladding, or silver. In certain embodiments, the side wall is made from gold. In certain embodiments, an adhesion layer 130, can be disposed between the underside of the side wall 110 and the substrate 120. The adhesion layer 130 can include a metal such as titanium, chromium, titanium oxide ($TiO_2$), chromium oxide ($Cr_2O_3$) or combinations thereof.

In certain embodiments, the nanoaperture can be immersed in a flow cell 105. The flow cell can contain an aqueous solution of a biomolecule of interest 160. A biomolecule of interest 160 can include a protein, DNA or RNA. Additional non-limiting examples of biomolecules 160 include those which associate with other molecules, such as ribosomes, polymerases, or other enzymes, protein-binding DNA sequences, riboswitches or ribozymes. The biomolecule of interest 160 can be labeled with one or more fluorophores. Non-limiting examples of fluorophores include Cy2, Cy3.1, Cy3.5, Cy35, Cy5.1, Cy5.5, Cy5, FITC, Fluorescein, GFP, RFP, YFP, BFP, CFP, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660 and Alexa Fluor 680. Incident light or illumination 180 can be shone from the bottom of the substrate 120 to create a light field concentrated near the bottom of the nanoaperture 101.

The nanoaperture 101 can also have a cross dimension D (width or diameter). The cross dimension D can depend on the wavelength of the incident light used for the nanoaperture. In certain embodiments, the cross dimension D can be a few hundred nanometers, for example, from about 20 nm to 500 nm, from about 50 nm to about 500 nm, from about 100 nm to about 500 nm, from about 150 nm to about 500 nm, from about 200 nm to about 500 nm, from about 250 nm to about 500 nm, from about 300 nm to about 500 nm, from about 350 nm to about 500 nm, from about 400 nm to about 500 nm, from about 450 nm to about 500 nm, from about 100 to about 300 nm, from about 100 to about 200 nm or from about 200 to about 250 nm. The nanoaperture can have various cross-sectional shapes, such as circular, elliptical, rectangular, oval, star-shaped, triangle, square, octagon, hexagon, multilateral, etc., or combinations thereof. For example, the nanoapertures can be circular in shape.

In certain embodiments, where the nanoaperture is a ZMW, the cross dimension D is less than the wavelength of the incident light used for the nanoaperture divided by 1.7. For example, and not by way of limitation, in certain embodiments where the incident light to be used has a wavelength of about 400 nm, a desired ZMW can have a cross dimension of less than or equal to about 235 mm. In certain embodiments where the incident light to be used has a wavelength of about 800 nm, a desired ZMW can have a cross dimension of less than or equal to about 470 nm. In certain embodiments, a ZMW nanoaperture can have a cross dimension from about 20 nm to about 400 nm, from about 20 nm to about 350 nm, from about 20 nm to about 300 nm, from about 20 am to about 250 nm, from about 20 nm to about 200 nm, from about 20 nm to about 150 nm, from about 20 nm to about 100 nm, from about 20 nm to about 500 nm, from about 100 nm to about 470 nm, from about 200 nm to about 470 nm, from about 300 nm to about 470 nm or from about 400 nm to about 470 nm. In certain embodiments, a ZMW of the present disclosure has a cross dimension D of less than or equal to about 470 nm.

The term "about" or "approximately" means within an acceptable error range for the particular value as determined by one of ordinary skill in the art, which will depend in part on how the value is measure or determine, i.e., the limitations of the measurement system. For example, "about" can mean a range of up to 20%, up to 10%, up to 5%, and or up to 1% of a given value.

In certain embodiments, the height (or thickness) H of the side wall 110 of the nanoaperture can be from about tens to about a few hundred nanometers. For example, and not by way of limitation, the height H can be from about 50 nm to about 500 nm, from about 100 nm to about 500 nm, from about 150 nm to about 500 nm, from about 200 nm to about 500 nm, from about 250 nm to about 500 nm, from about 300 nm to about 500 nm, from about 350 nm to about 500 nm, from about 400 nm to about 500 nm, from about 450 nm to about 500 nm, from about 100 to about 200 am, from about 100 to about 300 nm or from about 200 to about 300 nm.

In certain embodiments where the nanoaperture is a ZMW, a smaller height can reduce the effectiveness of the ZMW as gold can be transparent at very small thicknesses. However, the greater the height H, the more impedance for the biomolecule of interest 160 to diffuse to the bottom of the ZMW, which can reduce the sensitivity of the ZMW. Thus, a suitable height for the side wall 110 of the ZMW can be selected by balancing these considerations. In certain embodiments, a ZMW nanoaperture can have a height of about 100 to about 250 nm. In certain embodiments, where the ZMW geometrically confines the incident light to the about 0 nm to about 50 nm region of the bottom of the nanoaperture, the height of the side wall is greater than about 50 nm. For example, and not by way of limitation, the side wall height can be from about 100 nm to about 150 nm.

The side wall surface 112 of the nanoaperture 101 can be coated with a layer of a first functional molecule 115. In certain embodiments, the first functional molecule 115 can include a segment of polyethylene glycol (PEG) to provide a non-adsorption surface to inhibit non-specific adsorption of biomolecules onto the surface 112. In certain embodiments, the PEG can include about 1 to about 200 ethylene oxide ($CH_2CH_2O$) units, For example, the PEG can include about 1 to about 100 ethylene oxide units, about 1 to about 50 ethylene oxide units, about 1 to about 20 ethylene oxide units or about 1 to about 10 ethylene oxide units. In certain embodiments, the PEG can include about 3 ethylene oxide units.

In certain embodiments, the first functional molecule 115 can also include a group that can react with the surface of the side wall 112. For example, and not by way of limitation, the first functional molecule can include a thiol group, e.g., a terminal thiol group, which is reactive to the gold surface of the side wall 112. Upon suitable conditions, the thiol group of the first functional molecule 115 can react with the side wall surface 112 to form S—Au bonds to couple the molecule 115 with the side wall 112. For example, the molecule 115 can form a self-assembled monolayer (SAM) tethered on the side wall 112.

Figure 2A:
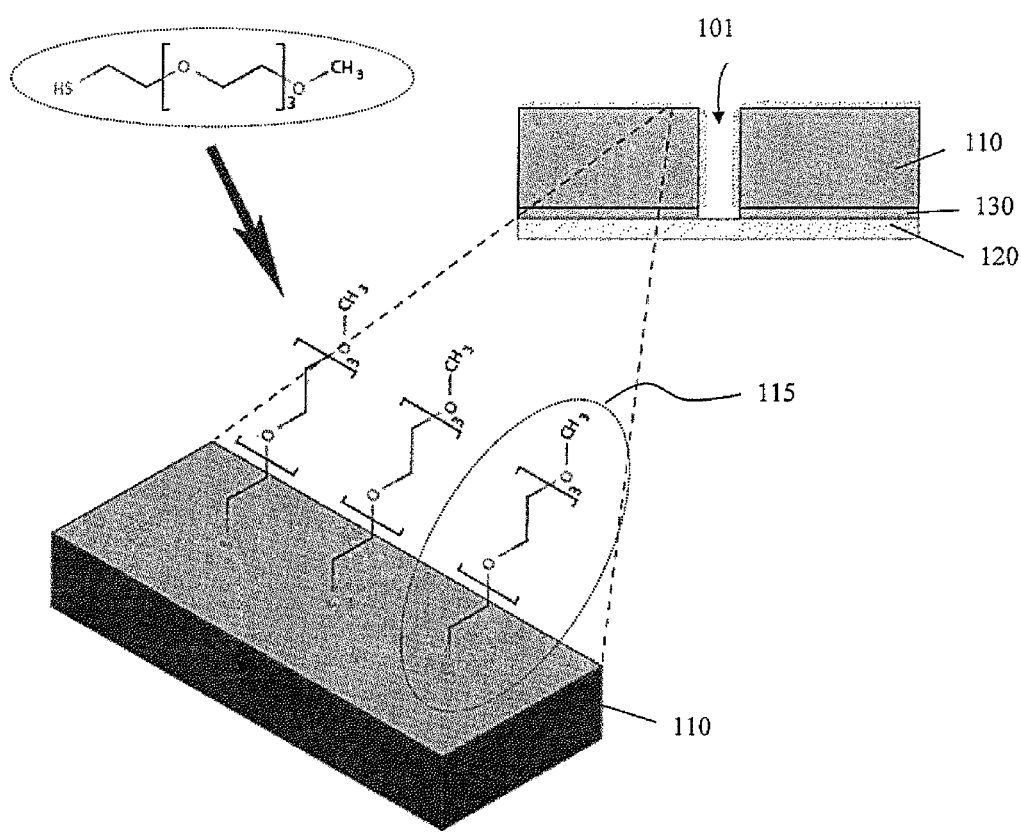
FIGS. 2A and 2B are schematic diagrams illustrating the passivation of the side wall of a nanoaperture and the passivation of the bottom surface of a nanoaperture according to some embodiments of the disclosed subject matter.

In certain embodiments, the first functional molecule 115 can further include non-PEG portions. For example, the first functional molecule can include a segment of polyalkylene group —$(CH_2)_x$— between the polyethylene glycol and the thiol group, where x can be from 1 to about 100. In certain embodiments, the x of —$(CH_2)_x$— is from about 2 to about 10. Referring to FIG. 2A, which schematically illustrates thiol-PEG passivation of the nanoaperture, in certain embodiments, the functional molecule $HSCH_2CH_2$ $(OCH_2CH_2)_3OCH_3$ can be used to passivate the gold surface of the side wall 110, including the top of the side wall and the surface of the side wall surrounding the nanoaperture 101.

In certain embodiments, the bottom surface 122 of the nanoaperture 101 can be functionalized with a non-adsorption or passivation layer (e.g., a monolayer) of at least one second functional molecule 125. In certain embodiments, the second functional molecule can include polyethylene glycol. For example, and not by way of limitation, the second molecule 125 can include about 1 to about 200 ethylene oxide ($CH_2CH_2O$) units, about 1 to about 100 ethylene oxide units, about 1 to about 50 ethylene oxide units, about 1 to about 20 ethylene oxide units, about 1 to about 10 ethylene oxide units, about 1 to about 100 ethylene oxide units, about 10 to about 200 ethylene oxide units, about 50 to about 200 ethylene oxide units or about 100 to about 200 ethylene oxide units.

In certain embodiments where the bottom surface 122 is glass, i.e., silica ($SiO_2$), the second functional molecule can include a silane group, e.g., a terminal silane group, and can be attached to the bottom surface via a Si—O—Si linkage. For example, the silane group can be attached to the bottom surface via condensation of a silicon oxide group of the silica to the silane, and is referred to herein as silane-PEG or PEG-Si.

Alternatively or additionally, the non-adsorption layer on the bottom surface 122 can include a second functional molecule that has a silane group, e.g., a terminal silane group, and a PEG component, as described above, and a moiety 126 capable of binding with a target biomolecule 150. The binding between the moiety 126 and the target biomolecule can be based on molecular recognition or affinity, e.g., ligand-receptor type binding. In certain embodiments, the second functional molecule can be biotinylated, i.e., include a biotin moiety. Such a molecule is herein referred to as silane-PEG-biotin or biotin-PEG-Si. In certain embodiments where the moiety is biotin, the target biomolecule 150 can be streptavidin. Alternatively or additionally, the second functional molecule can include other types of moieties such as glutathione, a hexahistidine tag, a FLAG tag and digoxigenin, which can bind to the target biomolecules glutathione S-transferase, an anti-his antibody, an anti-FLAG antibody and anti-digoxigenin, respectively.

In certain embodiments, the target biomolecule 150 can act as a linker group to which the biomolecule of interest 160 can bind. For example, in the case of streptavidin (as the target molecule), which includes 4 monomers that can each bind with a biotin molecule, the streptavidin can bind to both the second functional molecule 125 on the bottom surface 122 and the biomolecule of interest 160. Alternatively or additionally, the target molecule 150 can itself be fluorophore-labeled and become a subject of fluorescence study using the nanoaperture. Non-limiting examples of fluorophores are disclosed above.

Figure 2B:
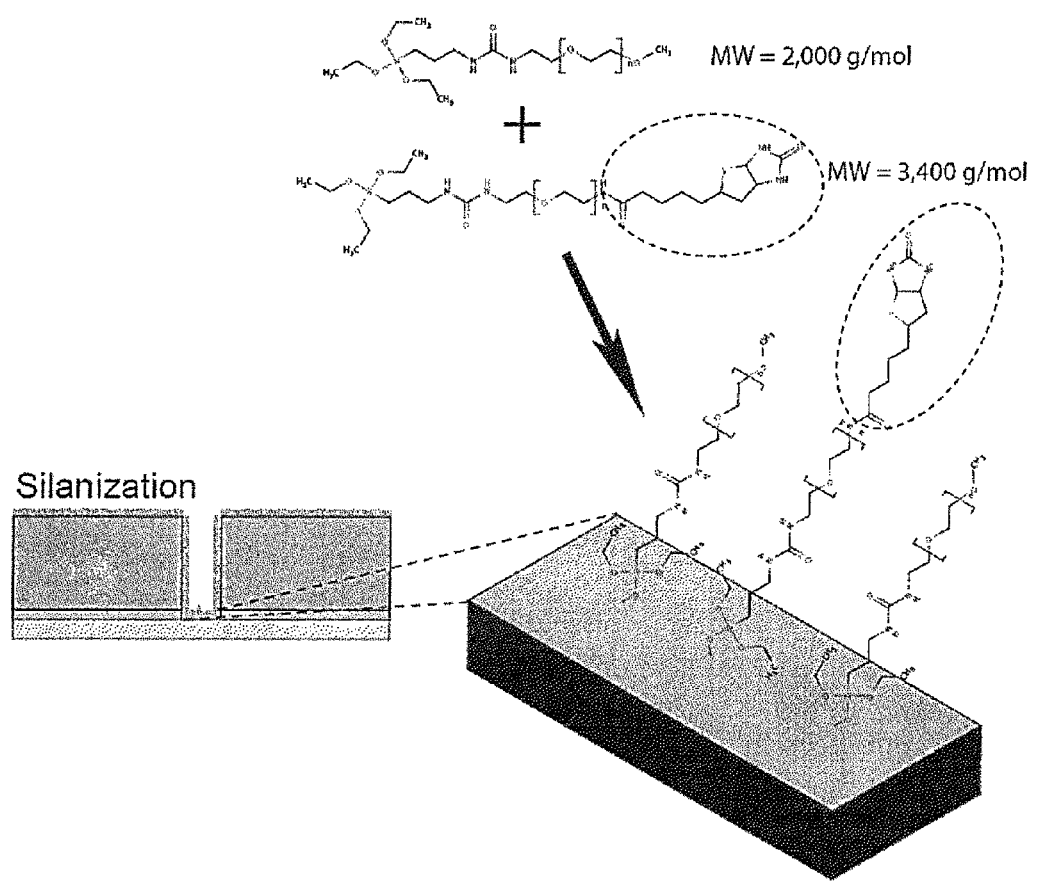

In certain embodiments, in order to observe or study single molecule fluorescence imaging using the nanoaperture, the non-adsorption layer can include a mixture of (1) a second functional molecule including polyethylene glycol and a moiety capable of binding with a target biomolecule, silane-PEG-biotin (illustrated in FIG. 1 by the slightly larger molecule having a triangle-shaped moiety 126); and (2) a second functional molecule including polyethylene glycol and no moiety capable of binding with the target biomolecule, e.g., silane-PEG (illustrated in FIG. 1 by the remaining molecules). For purposes of illustration and not limitation, FIG. 2B shows silanization of the bottom surface of the nanoaperture 101 using two different second functional molecules, silane-PEG, and silane-PEG-biotin. The molecular weights of the molecules shown in FIG. 2B are provided only as an example and not limiting.

By controlling the ratio of the (1) type molecule and (2) type molecule, e.g., selecting the ratio to be sufficiently small, the nanoaperture can contain a single (or 2, 3, 4, 5, 6, 7, 8, 9, 10 or more) target biomolecule 150 tethered onto the bottom surface via interaction or affinity binding with the moiety on the second functional molecule, and, therefore, a single (or 2, 3, 4, 5, 6, 7, 8, 9, 10 or more) biomolecule of interest 160 can be tethered in the detection volume of the nanoaperture. In certain embodiments, the ratio of the (1) type molecule and (2) type molecule can result in the nanoaperture containing zero target biomolecule, e.g., as a control. In certain embodiments, the ratio of the (1) type molecule to the (2) type molecule can be from about 1:1 to about 1:10,000. In certain embodiments, where the ratio of the (1) type molecule and (2) type molecule is large, e.g., 1:1, nanoapertures occupied by a single or small number of target biomolecules can be generated by the modification of the incubation time of the second functional molecule within the nanoaperture or the modification of the streptavidin concentration. In certain embodiments, the ratio of the (1) type molecule to the (2) type molecule can be about 1:1000.

Figure 3:
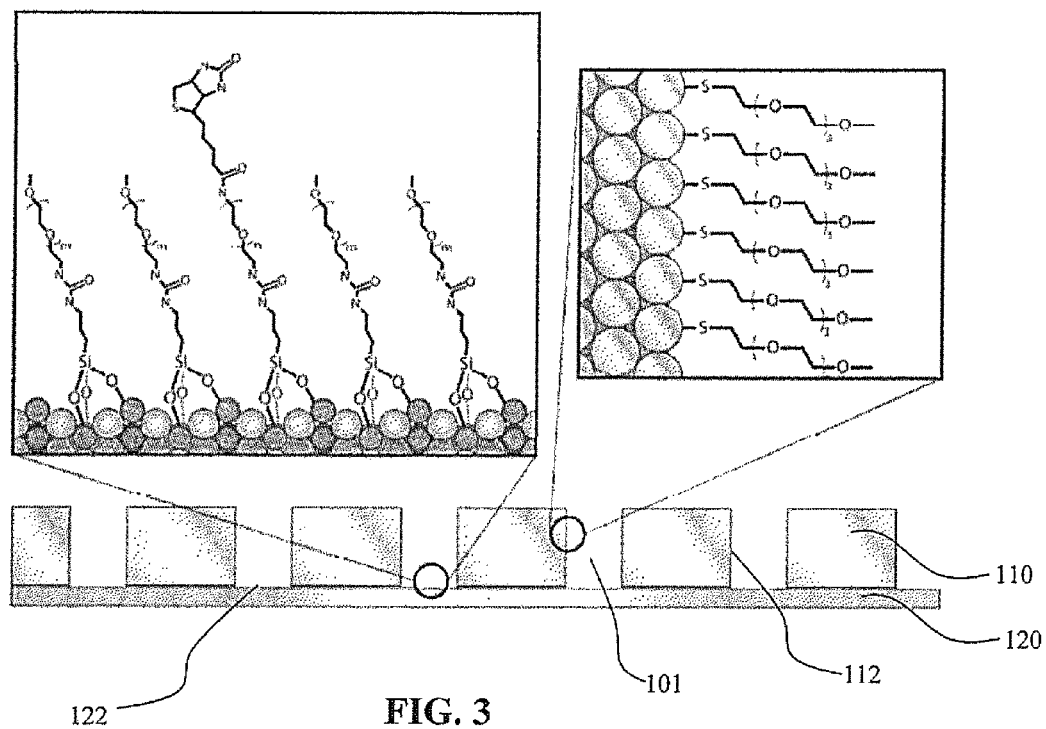
FIG. 3 shows molecular-level schematic diagram of thiol and silane passivated surfaces of a nanoaperture array. The gold surfaces of the nanoaperture arrays were passivated with a SAM formed using mPEG-SH, and the borosilicate surfaces of the nanoaperture arrays were passivated with a SAM formed using a binary mixture of biotin-PEG-Si and mPEG-Si.

The presently disclosed subject matter further provides nanoaperture arrays that include an array or matrix of the presently disclosed nanoapertures 101 separated by the side walls 110 on a substrate 120. For purposes of illustration and not limitation, FIG. 3 depicts a nanoaperture array according to an embodiment of the present disclosure. For example, and not by way of limitation, the nanoapertures present on the nanoaperture array can include zero-mode waveguides or nano-wells. In certain embodiments, the nanoaperture array can include two or more nanoapertures, e.g., ZMWs. In certain embodiments, the nanoaperture array can have about 2 to about 2,500,000,000 nanoapertures on the substrate 120. In certain embodiments, about 0.5%, about 1%, about 5%, about 10%, about 15%, about 20%, about 25%, about 30%, about 40%, about 50%, about 60%, about 70%, about 80%, about 90% or about 100% of the total area of the substrate has nanoapertures.

In certain embodiments, the nanoapertures of the nanoaperture array can be arranged in any manner. For example, and not by way of limitation, the nanoapertures can be arranged in parallel rows, in non-parallel rows, in branching patterns, in circular patterns, or combinations thereof. In certain embodiments, the nanoapertures of the nanoaperture array can be arranged randomly. In certain embodiments where a nanoaperture array contains two or more nanoapertures, the spacing between adjacent nanoapertures can be from about from about 0.5 nm to about 5 μm.

In another aspect, the disclosed subject matter provides a microfluidic device. The microfluidic device of the disclosed subject matter can include one or more nanoapertures or nanoaperture arrays, described above, on a support material. Non-limiting examples of a support material include glass, silica, quartz and silicon wafer. In certain embodiments, the support material can include a microscope slide. The microfluidic device can further one or more inlet ports coupled to the one or more nanoapertures or nanoaperture arrays. For example, and not by way of limitation, the microfluidic device can include one or more nanoaperture arrays that include two or more ZMWs.

In another aspect, the disclosed subject matter provides a method for fabricating the nanoapertures and nanoaperture arrays disclosed above. In certain embodiments of the method, a nanoaperture, e.g., a ZMW, having a bottom surface and a gold side wall can be formed on a substrate, as will be further discussed below. The dimensions and other characteristics of the nanoaperture have been described above. A surface of the side wall can be passivated with a first functional molecule including polyethylene glycol. In certain embodiments, the first functional molecule can include a thiol end group, and the passivating of the surface of the side wall can be accomplished by incubating the first functional molecule with the nanoaperture to form a S—Au bond coupling the first functional molecule with the gold surface.

The fabrication method can further include functionalizing the bottom surface of the nanoaperture with at least one second functional molecule including polyethylene glycol. In certain embodiments, the second functional molecule can include a silane end group, and the functionalizing can be accomplished by reacting the silane end group with the bottom surface to form a Si—O—Si bond coupling the second functional molecule with the bottom surface. The at least one second molecule can also include a mixture of silane-PEG molecules and silane-PEG-moiety molecules, where the moiety is capable of binding with a target biomolecule, as discussed above. In certain embodiments, the moiety can be a biotin moiety, and the target biomolecule can be streptavidin.

Figure 4A:
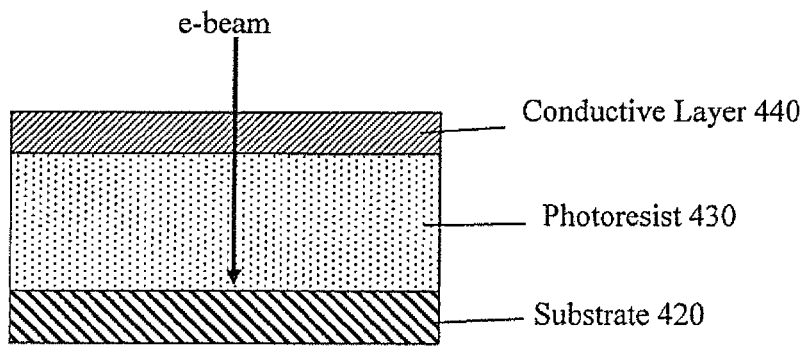
FIGS. 4A-4D are diagrams illustrating an example fabrication procedure of a nanoaperture according to some embodiments of the disclosed subject matter.
Figure 4B:
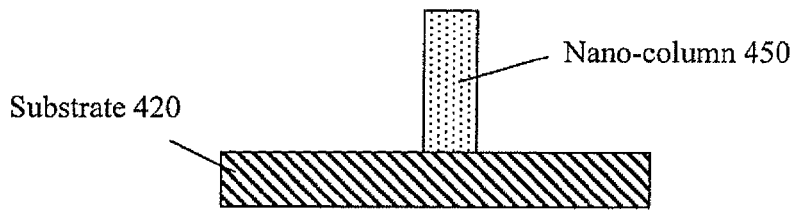
Figure 4C:
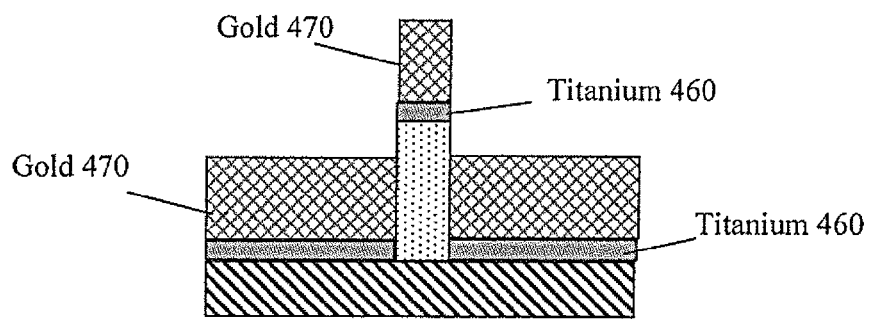
Figure 4D:
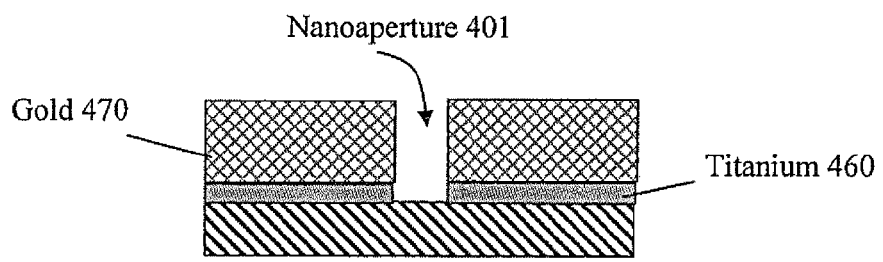
Figure 5:
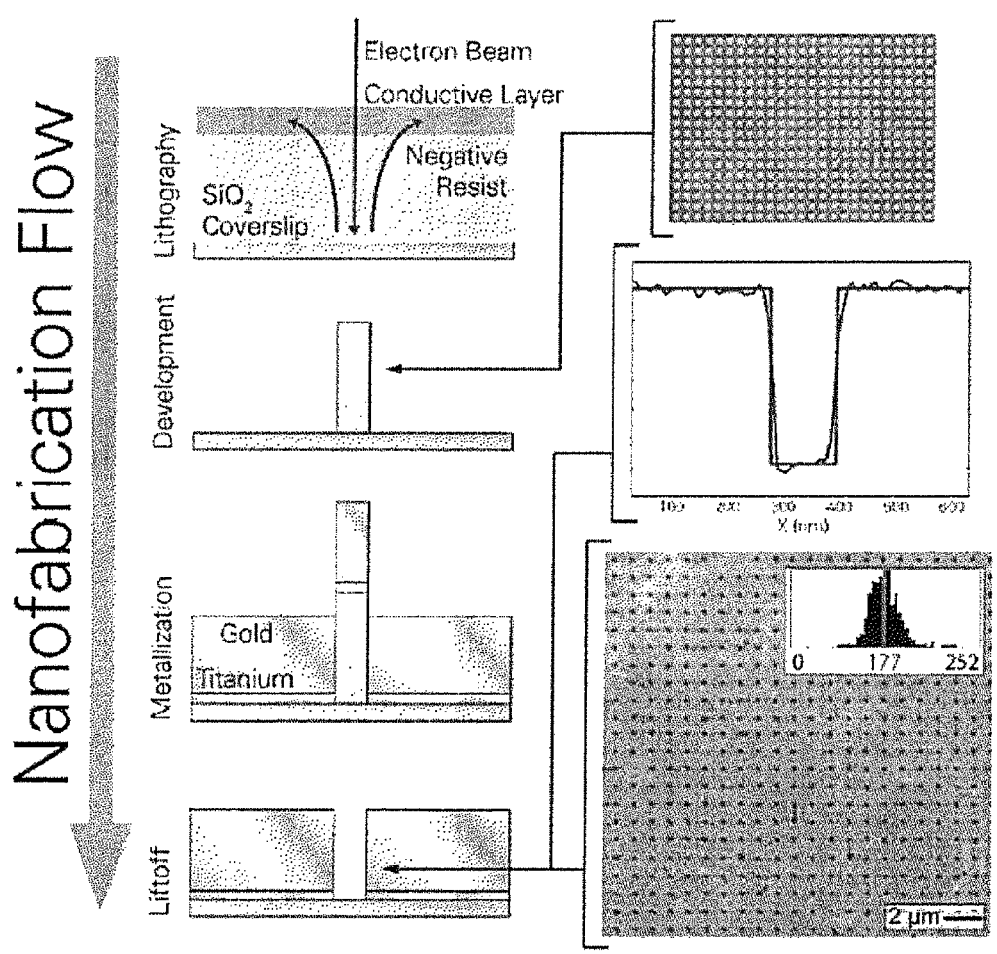
FIG. 5 shows a schematic diagram of one non-limiting embodiment of the nanoaperture fabrication process described herein.

For purposes of illustration and not limitation, FIG. 4 is a schematic representation of a method for fabricating a nanoaperture according to one embodiment of the disclosed subject matter (see also FIG. 5). In certain embodiments, a method of the disclosed subject matter can include applying a photoresist 430, e.g., a negative resist, on the surface of the substrate 420 (FIG. 4A). The photoresist material can include any molecule that polymerizes/cross-links upon application of UV light or an electron beam. Non-limiting examples of photoresist materials include poly(methyl methacrylate), the Ma-N 1400 series, Ma-N 2400 series, KMPR series, UVN-30, HNR series, DiaEtch series, NDS series, IC series, HR series, 125nXT series and the SU-8 series. In certain embodiments, the photoresist can include XR-1541-002, a hydrogen silsesquioxane negative resist. In certain embodiments, the photoresist layer 430 can include Ma-N 2403 from the Ma-N 2400 series. The photoresist layer can be applied to the substrate by any method known in the art that can produce a uniform layer of photoresist material. For example, and not by way of limitation, the photoresist layer can be applied by spin-coating.

In certain embodiments, the thickness of the photoresist layer is greater than the desired height of the nanoaperture. In certain embodiments, the photoresist layer can be from about 150 nm to about 2000 nm, from about 200 nm to about 2000 nm, from about 250 nm to about 2000 nm, from about 300 nm to about 2000 nm, from about 350 nm to about 2000 nm, from about 400 nm to about 2000 nm, from about 450 nm to about 2000 nm, from about 500 nm to about 2000 nm, from about 600 nm to about 2000 nm, from about 200 nm to about 500 nm, from about 200 nm to about 400 nm, from about 200 nm to about 300 nm, from about 150 nm to about 1000 nm, from about 150 nm to about 750 nm, from about 150 nm to about 600 nm, from about 150 nm to about 500 nm, from about 150 nm to about 450 nm, from about 150 nm to about 400 nm, from about 150 nm to about 350 nm, from about 150 nm to about 300 nm, from about 150 nm to about 250 nm or from about 150 nm to about 200 nm in thickness. For example, and not by way of limitation, the photoresist layer can be about 500 nm in thickness.

In certain embodiments, the method can further include applying a conductive layer 440, such as a conductive polymer, on top of the photoresist layer 430 (FIG. 4A). In certain embodiments, the conductive polymer can include poly(2,3-dihydrothieno-1,4-dioxin)-poly(styrenesulfonate) (PEDOT:PSS). In certain embodiments, the conductive layer can include aquaSAVE (Mitsubishi Rayon America Inc.). In certain embodiments, the conductive layer can include a metal such as, but not limited to, gold, silver, chrome, titanium, aluminum or a combination thereof. The conductive layer 440 can be applied to the substrate by any method known in the art that can produce a uniform layer of conductive material. For example, and not by way of limitation, the conductive layer 440 can be applied by spin-coating, and in the case of a metal conductive layer, the conductive layer can be applied by thermal deposition or electron beam deposition. In certain embodiments, the conductive layer can be from about 1 nm to about 500 nm in thickness. For example, and not by way of limitation, the conductive layer can be from about 1 nm to about 400 nm, from about 1 nm to about 300 nm, from about 1 ran to about 200 nm, from about 1 nm to about 100 nm, from about 1 nm to about 50 nm, from about 1 nm to about 40 nm, from about 1 nm to about 30 nm, from about 1 nm to about 20 nm, from about 1 nm to about 10 nm or from about 1 nm to about 5 nm. In certain embodiments, the conductive layer can be from about 1 nm to about 5 nm.

The method can further include, etching of a structure through exposure to a pattern of intense light to form a nano-column 450, also referred to herein as a cylindrical column (FIG. 4B). For example, the nano-column can be formed by the use of electron beam (e-beam) or ultraviolet lithography. In certain embodiments, the material surrounding the nano-column, e.g., non-crosslinked photoresist and conductive material, can be removed from the substrate, e.g., through mild agitation in a solution, to leave behind the nano-column on the substrate. In certain embodiments where a nanoaperture array is being fabricated, two or more nano-columns can be formed on the substrate to form two or more nanoapertures.

In certain embodiments, the method can include depositing a thin layer of metal 460 on the substrate 420 and the nano-column 450. The metal can include titanium, chromium or a combination thereof. In certain embodiments, the metal layer 460 can be from about 1 nm to about 10 nm in thickness. In certain embodiments, the metal layer 460 can be about 1 nm in thickness.

The method can further include depositing a layer of gold 470 onto the metal layer 460 to form the sidewall of the nanoaperture (FIG. 4C). The thickness of the gold layer will depend on the desired height of the sidewall of the nanoaperture. For example, and not by way of limitation, the gold layer can be from about 100 nm to about 300 nm in thickness. In certain embodiments, the gold layer 470 can be about 100 nm in thickness. The deposition of the metal layer 460 and the gold layer 470 can be by chemical vapor deposition or electron beam evaporation deposition, or other techniques known in the art. In certain embodiments, the nano-column 450, along with the titanium and gold layer deposited on top of it, can be removed, e.g., by sonication, to create the nanoaperture 401 (FIG. 4D).

Further details of the structure, fabrication and use of the above-described nanoapertures and nanoaperture arrays can be found in the following Examples, which are provided for illustration purposes only and not for limitation.

Example 1—Fabrication of Nanoapertures

Gold-based nanoapertures having aperture diameters ranging between 100-250 nm were fabricated on a nanoaperture array as follows (FIG. 2). Borosilicate coverslips (No. 1.5, VWR) were degreased in piranha solution (3:1 $H_2SO_4$: 30% $H_2O_2$) for 15 min, rinsed with Milli-Q ultrapure water, sonicated for 15 min in ethanol and then sonicated for 15 min in Milli-Q ultrapure water. Degreased coverslips were exposed to an $O_2$ plasma for 2 minutes, and a thin photoresist layer of Ma-N 2403 (negative resist; Micro Resist Technology GmbH), which is composed of a phenolic resin with a bisazide photoactive compound, was deposited with a spin coater onto the coverslips. Coverslip substrates were then prebaked at 90° C. for 1 minute, and a highly conductive polymer, 2.5% poly(2,3-dihydrothieno-1,4-dioxin)-poly(styrenesulfonate) (PEDOT:PSS), in $H_2O$, was filtered through a 0.2 μm Acrodisc syringe filter, deposited with a spin-coater as a conductive layer and then prebaked at 90° C. for 5 minutes.

Electron beam lithography was performed with a converted FEI Sirion SEM with a 30 kV electron beam, and was employed to pattern arrays of circles of diameters on the order of about 100 nm using the Nanometer Pattern Generation System (JC Nabity Lithography Systems). Electrons from the electron beam gun crosslinked the negative-tone resist, e.g., in the form of cylindrical columns within the negative resist, and excess charge was dissipated to a ground by the conductive layer.

Figure 16A:
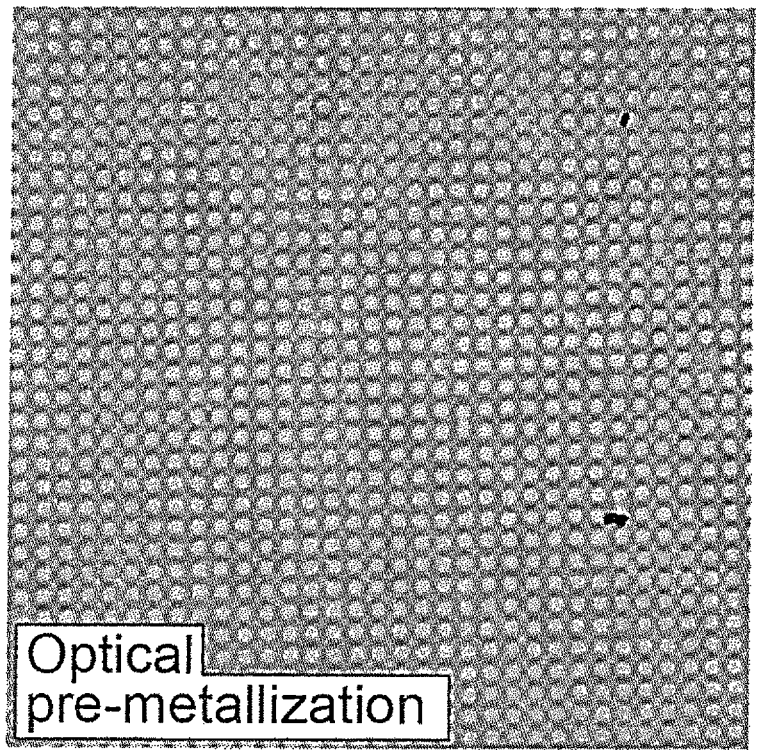
FIGS. 16A-16C are images of nanoapertures at different stages of an example fabrication procedure according to some embodiments of the disclosed subject matter.

In connection with the electron-beam lithography that can be used in this process, it was observed that the PEDOT:PSS conductive layer employed, which was applied to the Ma-N 2403 negative-tone resist in order to prevent charging during electron beam writing, failed to be completely removed by water washing following electron-beam writing. Without being bound to a particular theory, the conductive layer, which has a pH of 1.5-2.5 at room temperature, can potentially crosslink to the Ma-N 2403 negative-tone resist layer. Therefore, instead of washing with water, treatment with acetic acid, which would be expected to reverse the crosslinking equilibrium, was used to produce well-defined pillars. For example, the patterns were developed by immersion in 8.74 M acetic acid for 5 minutes, followed by mild agitation in Milli-Q ultrapure water and mild agitation in ethanol, leaving behind cylindrical columns having a height of approximately 500 nm. Optical micrographs of the cylindrical column (nano-column) patterns are shown in FIG. 16A and FIG. 5, top panel.

Atop these columns, an optically transparent layer of 1 nm or 50 Å of titanium was deposited with an electron beam gun using an Angstrom EvoVac Deposition System to increase the adhesion of gold to the substrate. Approximately 100 nm of gold was then deposited in a similar fashion, such that the metallization process did not cover the entire height of the patterned columns, leaving the columns exposed to solvent. Sonication in extremely basic, aqueous solution of 1M KOH for 2 minutes induced liftoff of the columns, removing residual photoresist and forming nanoapertures in the relief.

The nanoapertures on the array were characterized with an Agilent 8500 FE-SEM and Digital Instruments atomic force microscopy (AFM) and ImageJ. Approximately 78% of the fabricated patterns were geometrically identified to be ZMW nanoapertures having an average diameter of about 177±16 nm (1σ, n=499), with a relatively narrow diameter distribution, and a spacing of 1-5 μm (FIG. 5, bottom panel). The top panel of FIG. 5 shows a wide-field, optical microscope image of a pre-metallization pillar array, and the middle panel of FIG. 5 shows an atomic force microscope image cross-section of a typical nanoaperture; the red line is a boxcar function fit with a 115 nm length.

Figure 16B:
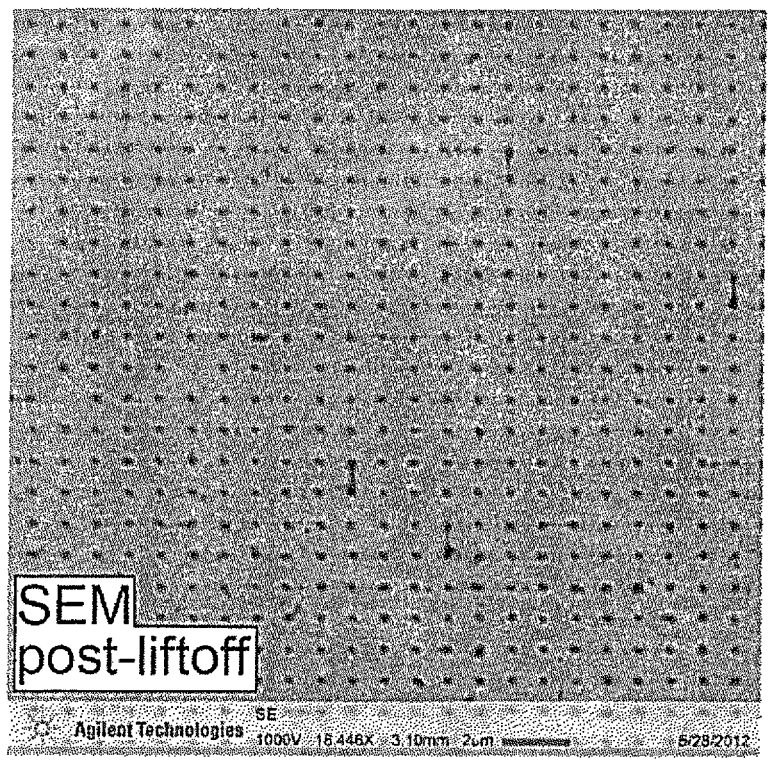
Figure 16C:
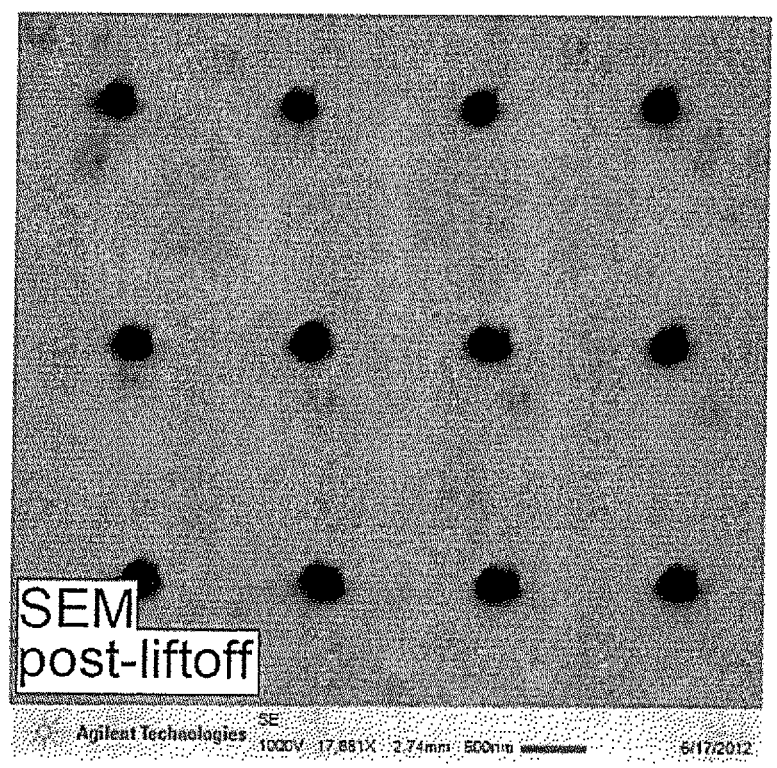

SEM micrographs of the individual nanoapertures, including arrays of nanoapertures, are shown in FIG. 16B and FIG. 16C (which is an enlarged image of a portion of FIG. 16B). These nanoapertures exhibit both the strong electromagnetic confinement responsible for the reduction in excitation volume as well as the gold surface plasmon-mediated fluorescence enhancement that is characteristic of smaller diameter gold nanoapertures (Wenger, J. et al., Opt. Express, 16:3008 (2008); Gerard, D. et al., Phys. Rev. B, 77:045413 (2008)).

Example 2—Passivation of the Nanoapertures

The nanoapertures fabricated by Example 1 were passivated to reduce non-specific adsorption to the surface of the nanoapertures. As silanes have a propensity to covalently bond to gold, thiolation of the gold cladding was performed prior to silanization of the silica nanoaperture bottoms to yield more homogeneously passivated nanoapertures. The passivation procedure started with cleaning the nanoapertures in 1.5 hour aged piranha solution (3:1 $H_2SO_4$:30% $H_2O_2$), followed by a short treatment by oxygen plasma. The cleaned nanoapertures were then incubated in 5 mM or 1 mM anhydrous ethanolic solutions of methoxy-terminated, thiol-derivatized PEG (PEG-SH; MW=350 g/mol) (Nanocs, Boston, Mass.) for 12 hours to thiolate the gold surfaces to ensure sufficient time for SAM formation, and then rinsed thoroughly in EtOH and dried with $N_2$. Silanization was performed by mixing a predetermined molar ratio of biotin-terminated, triethoxy-functionalized, silane-derivatized PEG (biotin-PEG-Si—$(OCH_3)_3$; MW=3400 g/mol) to methoxy-terminated, triethoxyfunctionalized, silane-derivatized PEG (mPEG-Si—$(OCH_3)_3$; MW=2000 g/mol) (Laysan Bio Inc., Arab, Ala.) (as shown in FIGS. 2A and 2B) in anhydrous toluene, with 10 mM glacial acetic acid such that the total concentration of silane was on the order of 100 μM. The nanoapertures were incubated in the silane solution for 24 hours, rinsed with distilled, deionized water for 15 minutes, rinsed with ethanol or isopropyl alcohol and blown dry with $N_2$.

Example 3—Fluorescent Microscopy of Cy3- and Cy5-Labeled Bio-RF1$_{S192C,E256C}$ To assess the robustness of the gold nanoaperture passivation methodology described herein, nanoaperture fluorescence microscopy experiments were performed using a biotinylated, Cy3 FRET donor- and Cy5 FRET acceptor-labeled, double-cysteine RF1$_{S192C,E256C}$ mutant of the *Escherichia coli* RF1.

Figure 6:
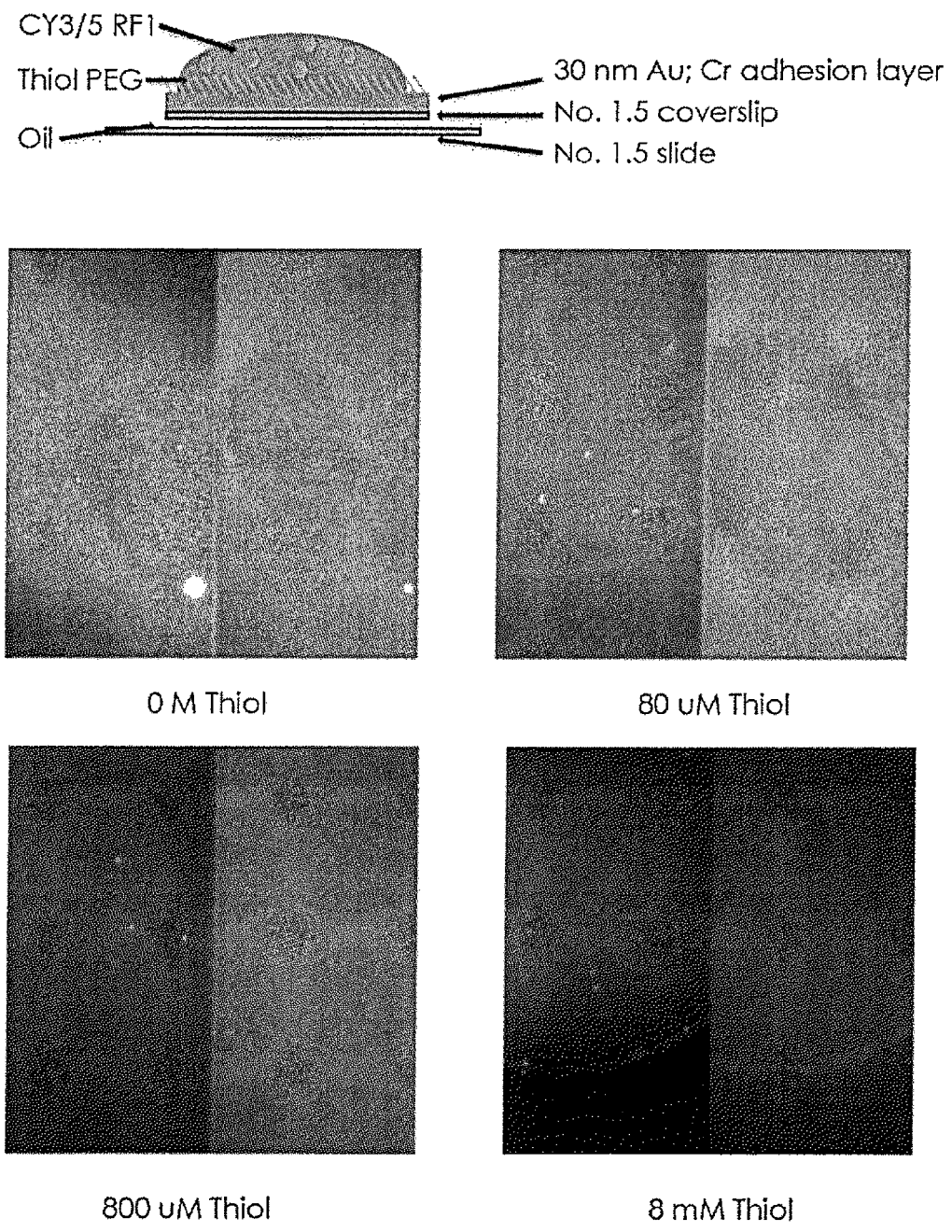
FIG. 6 is a schematic cross sectional view of a test setup for passivating a gold surface using a thiol-PEG molecule and depicts fluorescence images of a fluorophore-labeled protein, Cy3- and Cy5-labeled bio-RF1$_{S192C,E256C}$ as applied on a gold surface passivated with different concentrations of thiol-PEG.

Fluorescently labeled release factor 1 (RF1) which catalyzes nascent polypeptide chain release during the termination stage of protein synthesis by the ribosome, was used as a fluorophore (Cy3 and Cy5)-labeled test biomolecule of interest. All cysteine residues native to RF1 were mutated to serine (C51S, C201S, C257S), and two cysteine residues were introduced at positions of a distance of approximately 40 Å apart (S192C, E256C), all using site-directed mutagenesis. These two cysteine residues were labeled with Cy3- and Cy5-maleimides at the reactive sulfhydryl groups, and purified using fast protein liquid chromatography (FPLC). A biotin molecule was covalently attached to the protein with a biotin ligase to generate Cy3- and Cy5-labeled bio-RF1$_{S192C,E256C}$. FIG. 6, top panel, shows a schematic of the test. A solution containing Cy3- and Cy5-labeled bio-RF1$_{S192C,E256C}$ was placed upon an optically transparent layer of gold that was passivated with thiolated PEG. This surface was imaged with a single molecule fluorescence microscope in epi-fluorescence mode. FIG. 6, bottom two panels, show images captured with the microscope of gold surfaces treated with various concentrations of thiol-PEG to form SAMs. It can be seen that even at concentrations greater than 80 µM, non-specific binding appears negligible, as indicated by the significant decrease in fluorescence intensity on both the left-hand side (Cy3 fluorescence intensity) and the right-hand side (Cy5 fluorescence intensity) of the images.

Example 4—Generation of Cy3- and Cy5-Labeled Bio-RF1$_{S167C,E256C}$

Cy3 FRET donor- and Cy5 FRET acceptor-labeled, double-cysteine mutant of the Escherichia coli RF1, RF1$_{S167C,E256C}$, was generated for use in several single molecule fluorescent microscopy experiments.

The Escherichia coli (E. coli) prfA gene encoding wild type poly peptide chain termination factor 1 (RF1) was previously cloned into the pPROEX-HTb expression vector (Life Technologies, Inc.) downstream of an N-terminal hexa-histidine affinity purification tag and a Tev protease cleavage site. Additionally, all native cysteines were removed and a single cysteine was introduced at amino acid position 167 with a serine-to-cysteine mutation (RF1$_{S167C}$) using site-directed mutagenesis. Starting with this RF1$_{S167C}$ construct, an N-terminal enzymatic biotinylation tag (GLN-DIFEAQKIEWHE) was subcloned downstream of the Tev protease cleavage site, and site-directed mutagenesis was used to introduce a glutamic acid-to-cysteine mutation at amino-acid position 256 (bio-RF1$_{S167C,E256C}$) to generate a RF1 protein having two cysteines at a distance of approximately 30 Å apart.

RF1 proteins were overexpressed in E. coli cells, purified using affinity chromatography, Tev protease treated and purified away from the cleaved hexa-histidine tags and Tev protease using previously published protocols. Briefly, electro-competent BL21(DE3) E. coli cells cotransfected with pPROEX-HTb expression vectors carrying either RF1$_{S167C}$ or bio-RF1$_{S167C,E256C}$ and pET-26b(+) expression vectors carrying the gene prmC, a methyltransferase that modifies RF1, were grown under ampicillin and kanamycin selection, and RF1 protein overexpression was induced by addition of 1 mM isopropyl β-D-1-thiogalactopyranoside. Cells were lysed with a French Press, and RF1 proteins were purified using affinity chromatography with a Ni-NTA agarose bead column. Purified RF1 proteins were subsequently incubated with hexa-histidine-tagged Tev protease overnight, and the proteolyzed RF1 proteins were purified from the cleaved hexa-histidine tags and the hexa-histidine-tagged Tev protease using a second passage through a Ni-NTA agarose bead column. Bio-RF1$_{S167C,E256C}$ was biotinylated to generate using recombinant E. coli BirA biotin-ligase (plasmid obtained from AddGene) that was overexpressed, purified and used following a previously published protocol.

The RF1 proteins were then fluorescently labeled. For protein labeling of the RF1 proteins, cysteine 167 in RF1$_{S167C}$ was as reduced by incubation with 1 mM tris (2-carboxyethyl) phosphine hydrochloride at room temperature and labeled by reaction with 15× molar excess of maleimide-derivatized Cy5 using a previously published protocol. Bio-RF1$_{S167C,E256C}$ was reduced and labeled following a similar protocol, but using equivalent concentrations of both maleimide-derivatized Cy3 and Cy5. Labeled RF1 proteins were purified from unreacted dyes using size-exclusion column chromatography with a HiLoad 16/600 Superdex 75 pg chromatography column (GE Lifesciences), and were subsequently purified from unlabeled RF1 proteins using hydrophobic interaction column chromatography with a TSKgel Phenyl-5PW column using previously published protocols. The purification yielded pure, 100% Cy5-labeled RF1$_{S167C}$ (RF1$_{Cy5}$) and pure, 100%, 1:1 stoichiometrically Cy3- and Cy5-labeled bio-RF1$_{S167C,E256C}$.

Example 5—Fluorescent Microscopy of RF1$_{S167C,E256C}$

To further assess the effectiveness of the nanoapertures described herein, additional fluorescence microscopy experiments were performed using the biotinylated, Cy3 FRET donor- and Cy5 FRET acceptor-labeled, double-cysteine mutant of the Escherichia coli RF1, RF1$_{S167C,E256C}$, described above in Example 4.

Flow cells were prepared for imaging by incubation with ultrapure bovine serum albumin (Ambion) and a 50-nucleotide oligomer of random-sequence duplex DNA, and, when specified, a subsequent incubation with 1 M streptavidin using a previously published protocol. Cy3- and Cy5-labeled bio-RF1$_{S167C,E256C}$ was diluted to the specified concentration in a Tris-polymix buffer, loaded into the flow cells, incubated for 5 min at room temperature, and untethered Cy3- and Cy5-labeled bio-RF1$_{S167C,E256C}$ was removed by washing the flow cells with 200 µl of Tris-polymix buffer. The tris-polymix buffer included 50 mM Tris-acetate (pH at 25° C.=7.0), 100 mM KCl, 5 mM ammonium acetate, 0.5 mM calcium acetate, 0.1 mM EDTA, 10 mM 2-mercaptoethanol, 5 mM putrescine, 1 mM spermidine, 15 mM magnesium acetate and 1% (w/v) β-D-glucose. Immediately prior to imaging, flow cells were washed and filled with Imaging buffer, and, when specified, various concentrations of Cy5-labeled RF1$_{S167C}$. The Imaging buffer included Tris-polymix buffer supplemented with 300 mg/ml glucose oxidase, 40 mg/ml catalase, 1 mM 1,3,5,7-cyclooctatetraene (Sigma-Aldrich) and 1 mM p-nitrobenzyl alcohol.

Figure 7:
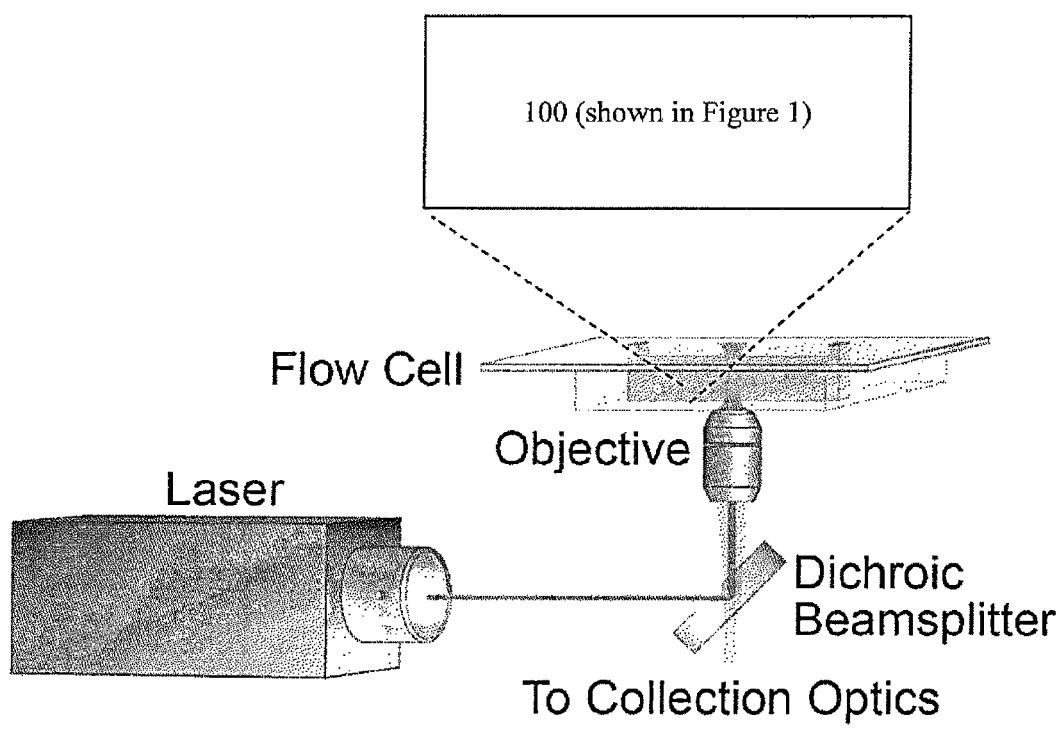
FIG. 7 is a diagram of an example test setup for fluorescence imaging using nanoapertures of the disclosed subject matter.

Passivated nanoaperture arrays, of which a majority were geometrically characterized as ZMWs, as described in Example 1, were used in fluorescence imaging of Cy3- and Cy5-labeled bio-RF1$_{S167C,E256C}$. A schematic setup of the fluorescence measurement is shown in FIG. 7. The nanoapertures were illuminated through a Nikon, water-immersion 60×NA=1.2 PlanApo objective using a 50 mW, 532 nm diode-pumped solid-state laser (CrystaLaser) through a 552 nm, single-edge dichroic beamsplitter and a downstream 533 nm (FWHM=17 nm) notch filter (Thorlabs) using a Nikon Ti—U inverted microscope. Fluorescence emissions were collected through the objective, and imaged through a Photometrics DV2 wavelength splitter containing a 630dcxr dichroic beamsplitter, and HQ575/40 m and HQ680/50 m emission filters (for Cy3 and Cy5, respectively) onto a 512×512 pixel Andor iXon3 897E electron multiplying charge-coupled-device camera. Movies were recorded at a 100 ms acquisition rate, 14-bit ADC, 10 MHz horizontal shift, 3.33 MHZ vertical shift and a linear EM gain of 200 and without binning using Metamorph software.

All analyses was performed with Python using NumPy and SciPy, Matplotlib, and the Python Imaging Library. Individual. Cy3 or Cy5 intensity versus time trajectories were constructed by selecting those pixels on the Cy3 half of the initial frame with intensities exceeding three standard deviations of the mean pixel intensity, clustering neighboring pixels into regions, calculating the center of mass (COM) of each region, and mapping those COM coordinates onto the Cy5 half of the frame when applicable. The intensity of a region in each frame of a movie was then obtained by summing the four pixels neighboring the region COM, linearly scaled by distance to the COM, such that the total pixel area employed in the sum was one pixel. The x- and y-coordinates for each region COM were drift-corrected in each frame of each movie by the drift of the COM of the entire illumination profile in that movie Flow cells were prepared for imaging by incubation with ultrapure bovine serum albumin (Ambion) and a 50-nucleotide oligomer of random-sequence duplex DNA, and, when specified, a subsequent incubation with 1 M streptavidin. Cy3- and Cy5-labeled bio-RF1$_{S167C,E256C}$ was diluted to the specified concentration in a Tris-polymix buffer, loaded into the flow cells, incubated for 5 min at room temperature to anchor Cy3- and Cy5-labeled bio-RF1$_{S167C,E256C}$ to the bottom of the nanoapertures via conjugation to a streptavidin molecule which had previously been conjugated to a biotin at the bottom of each nanoaperture. Untethered Cy3- and Cy5-labeled bio-RF1$_{S167C,E256C}$ was removed by washing the flow cells with 200 µl of Tris-polymix buffer. The Tris-polymix buffer included 50 mM Tris-acetate (pH at 25° C.=7.0), 100 mM KCl, 5 mM ammonium acetate, 0.5 mM calcium acetate, 0.1 mM EDTA, 10 mM 2-mercaptoethanol, 5 mM putrescine, 1 mM spermidine, 15 mM magnesium acetate and 1% (w/v) 3-D-glucose. Immediately prior to imaging, flow cells were washed and filled with Imaging buffer, and, when specified, various concentrations of Cy5-labeled RF1$_{S167C}$. The imaging buffer included Tris-polymix buffer supplemented with 300 mg/ml glucose oxidase, 40 mg/ml catalase, 1 mM 1,3,5,7-cyclooctatetraene (Sigma-Aldrich) and 1 mM p-nitrobenzyl alcohol.

Spots were chosen after thresholding a background corrected image to three standard deviations above the mean intensity in the Cy3 channel of the DV2. These coordinates were monitored in the Cy3 channel and translated into their corresponding spot on the Cy5 channel by tracking the center of mass of the entire image to correct for drift, and applying this correction to the location of the particle spot of interest at each frame. Intensities were summed area-dependently upon the neighboring four pixels, such that the total spot area was one pixel. Single-process photobleaching events were located by convoluting the signal with a function reminiscent of a negative, odd-valued (v=1) harmonic oscillator wavefunction, thresholding this to +3σ, and then locating local maxima.

Figure 8:
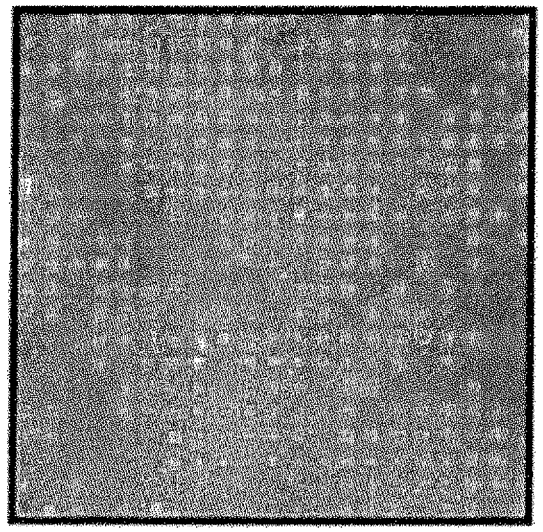
FIG. 8 shows a fluorescence image of the test protein Cy3- and Cy5-labeled bio-RF1$_{S167C,E256C}$ as applied on the nanoapertures of the disclosed subject matter (top panel), and a fluorescent image of the Cy3- and Cy5-labeled bio-RF1$_{S167C,E256C}$ as applied on a bulk silicon substrate as a comparison (bottom panel).
Figure 8:
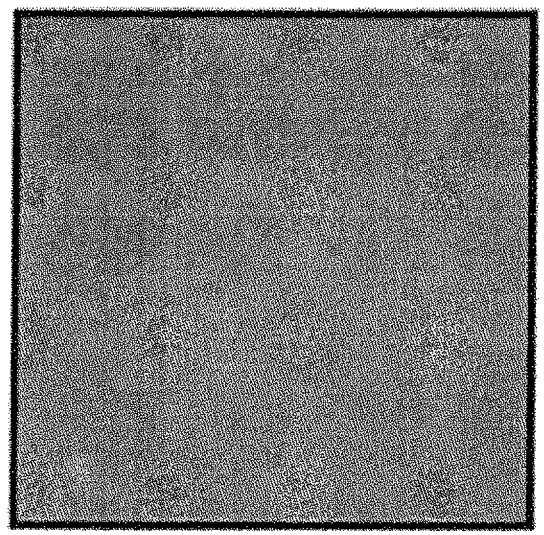

The ability to specifically localize a biotinylated target biomolecule from solution to the silica bottom of a nano-aperture is dependent upon the formation of a biotin-strepta-vidin-biotin bridge between the biotin-PEG-Si on the silica bottom of the nanoaperture, streptavidin and the biotinylated target biomolecule, e.g., Cy3- and Cy5-labeled bio-RF1$_{S167C,E256C}$. After incubation of a flow cell with 1 µM streptavidin for 5 minutes at room temperature, washing with Tris-polymix buffer, incubation with 1 pM Cy3- and Cy5-labeled bio-RF1$_{S167C,E256C}$ for 5 minutes at room temperature, and washing with Imaging buffer, wide-field fluorescence imaging of the flow cell yielded fluorescence emission from Cy3- and Cy5-labeled bio-RF1$_{S167C,E256C}$ in a well-defined pattern corresponding to the nanoaperture array (FIG. 8, top panel).

When performing the same experiment in a neighboring flow cell, but in the absence of streptavidin, no fluorescence emission was detected from the nanoaperture array. Even imaging of regions of bulk silica just proximal to the nanoaperture array revealed only minimal fluorescence emission from spatially localized Cy3- and Cy5-labeled bio-RF1$_{S167C,E256C}$ (FIG. 8, bottom panel). This was attributed to the nonspecific adsorption of Cy3- and Cy5-labeled bio-RF1$_{S167C,E256C}$ to defects in the borosilicate surface of the coverslip substrate (FIG. 8, bottom panel). Thus, the passivating SAMs resisted the non-specific adsorption of Cy3- and Cy5-labeled bio-RF1$_{S167C,E256C}$ to both the gold side wall of the nanoaperture and the silica bottoms of the gold nanoaperture arrays, while the presence of streptavidin at the bottom of the nanoaperture arrays allowed the specific localization of Cy3- and Cy5-labeled bio-RF1$_{S167C,E256C}$ to the nanoaperture arrays. In addition to demonstrating the robustness of the SAM-based passivation scheme, these results show that the presence of neither the gold side walls nor the mPEG-SH SAMs interfered with passivation of the silica regions of the substrates with the biotin-PEG-Si and mPEG-Si SAMs.

The biotin-PEG-Si that is responsible for localizing streptavidin, and therefore localizing Cy3- and Cy5-labeled bio-RF1$_{S167C,E256C}$ molecules, to the silica nanoaperture bottoms via a biotin-streptavidin-biotin bridge can be Poisson-distributed throughout the nanoapertures. Thus, whereas individual nanoapertures can contain zero, one, two, three, or more surface-tethered Cy3- and Cy5-labeled bio-RF1$_{S167C,E256C}$ molecules, the exact distribution that is observed is dependent upon the ratio of biotin-PEG-Si to mPEG-Si employed during passivation. For example, the larger the ratio, the greater the probability of observing multiple surface-tethered Cy3- and Cy5-labeled bio-RF 1$_{S167C,E256C}$ molecules per nanoaperture.

Figure 12:
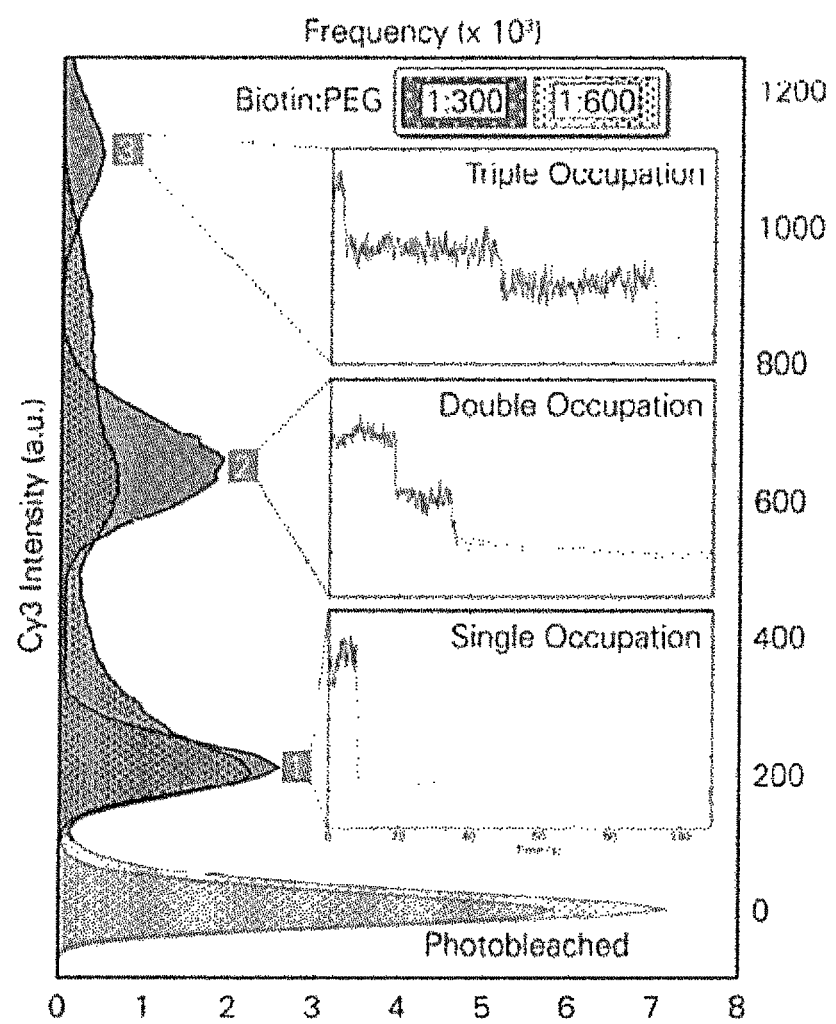
FIG. 12 shows tunable nanoaperture occupation. Histograms show the distributions of Cy3 fluorescence intensities observed over 100 seconds from nanoapertures in flow cells that had been passivated with a 1:300 or a 1:600 ratio of biotin-PEG-Si:mPEG-Si and then incubated with both bio-RF1$_{S167C,E256C}$ and streptavidin. Insets show discrete photobleaching events in Cy3 fluorescence intensity versus time trajectories that contribute to the histogram peaks and correspond to the occupancy of bio-RF1$_{S167C,E256C}$ in individual nanoapertures

To demonstrate this tunable control over nanoaperture occupation, the Cy3 fluorescence emission from single nanoapertures containing surface-tethered Cy3- and Cy5-labeled bio-RF1$_{S167C,E256C}$ was characterized in flow cells that have been passivated using the passivation scheme described in Example 2 with particular ratios of biotin-PEG-Si to mPEG-Si. Normalized histograms were constructed of the intensity of Cy3 fluorescence emitted from individual nanoapertures in flow cells passivated with 1:600 ratio (n=173, where n is the number of nanoapertures that were characterized) and 1:300 ratio (n=195) of biotin-PEG-Si:mPEG-Si that were both incubated with 1 µM streptavidin for 5 minutes at room temperature, washed with Tris-polymix buffer, incubated with 100 nM Cy3- and Cy5-labeled bio-RF1$_{S167C,E256C}$ for 5 minutes at room temperature, and washed with Imaging buffer (FIG. 12). As expected, the distributions of the average Cy3 fluorescence intensity per nanoaperture are resolved into discrete peaks that correspond to discrete numbers of Cy3- and Cy5-labeled bio-RF1$_{S167C,E256C}$ molecules per nanoaperture.

Figure 9A:
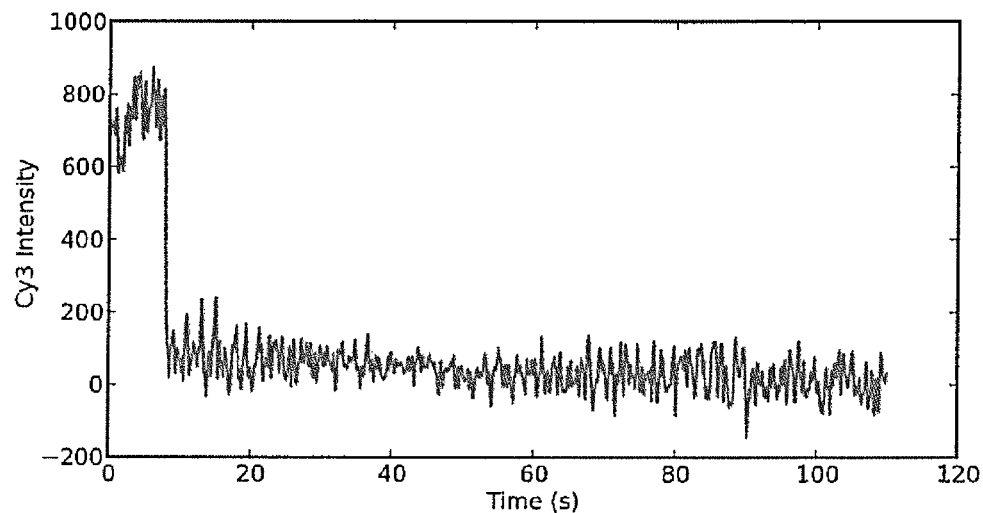
FIGS. 9A-9C are fluorescence intensity time traces indicating photobleaching of Cy3- and Cy5-labeled bio-RF1$_{S167C,E256C}$ in different nanoapertures of gold-based passivated nanoapertures.
Figure 9B:
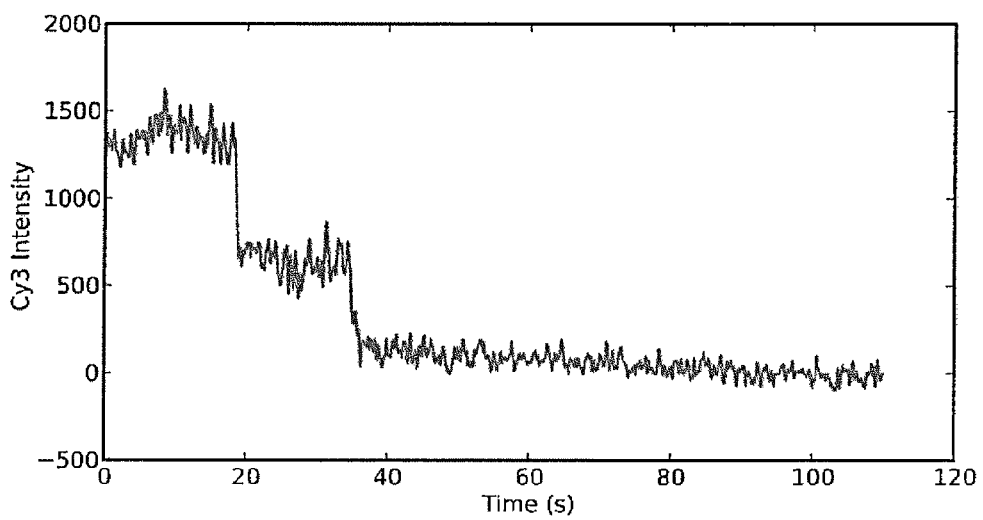
Figure 9C:
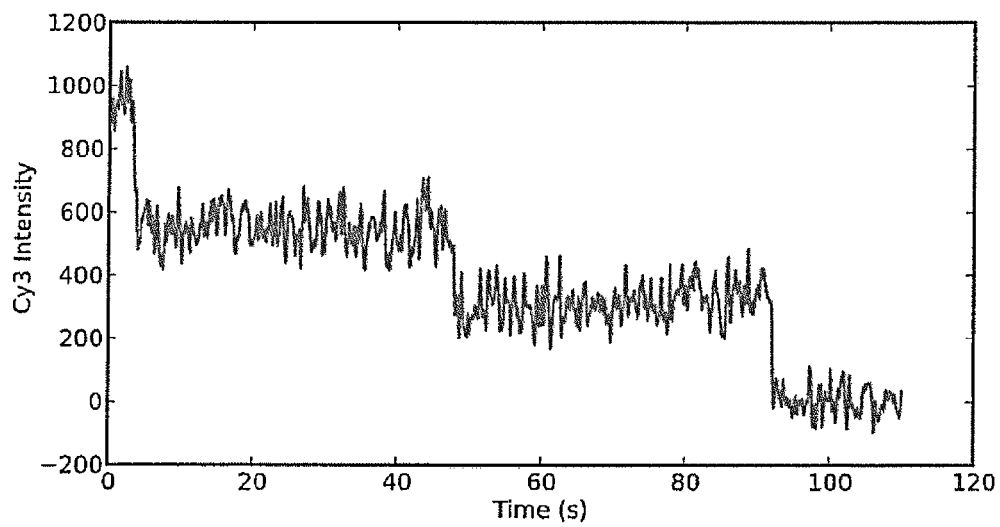
Figure 10A:
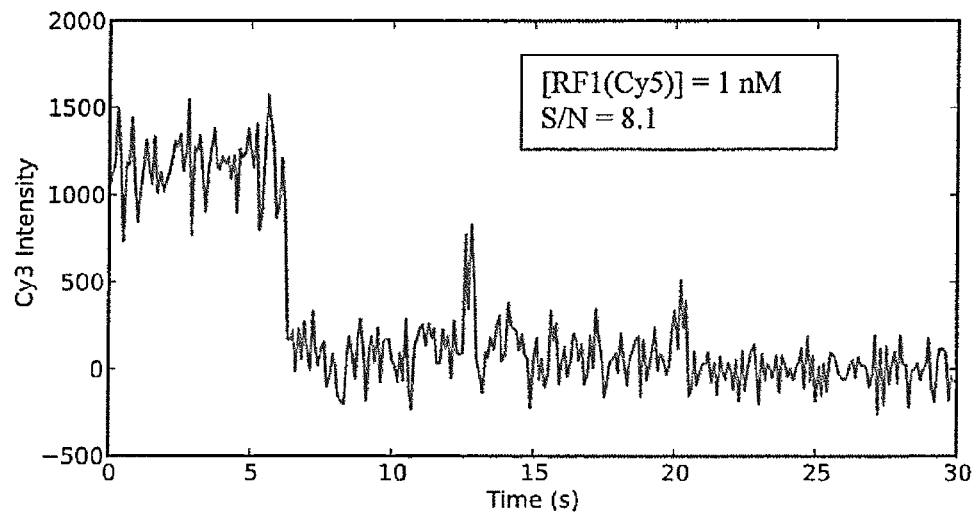
FIGS. 10A-10D are fluorescence intensity time traces and the corresponding signal-to-noise ratios (S/Ns) for Cy3- and Cy5-labeled bio-RF1$_{S167C,E256C}$ at different concentrations of bio-RF1$_{S167C}$ as a test biomolecule in the background of the nanoapertures according to the disclosed subject matter.
Figure 10B:
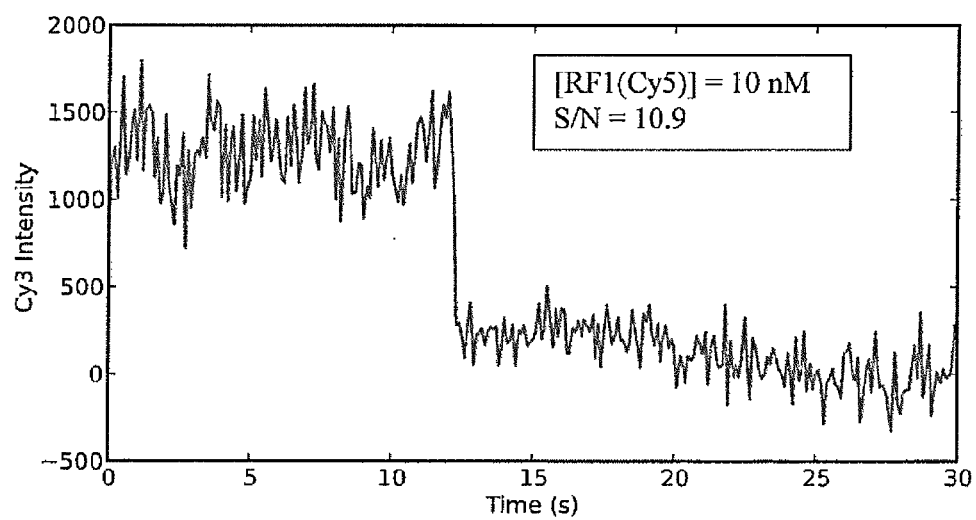
Figure 10C:
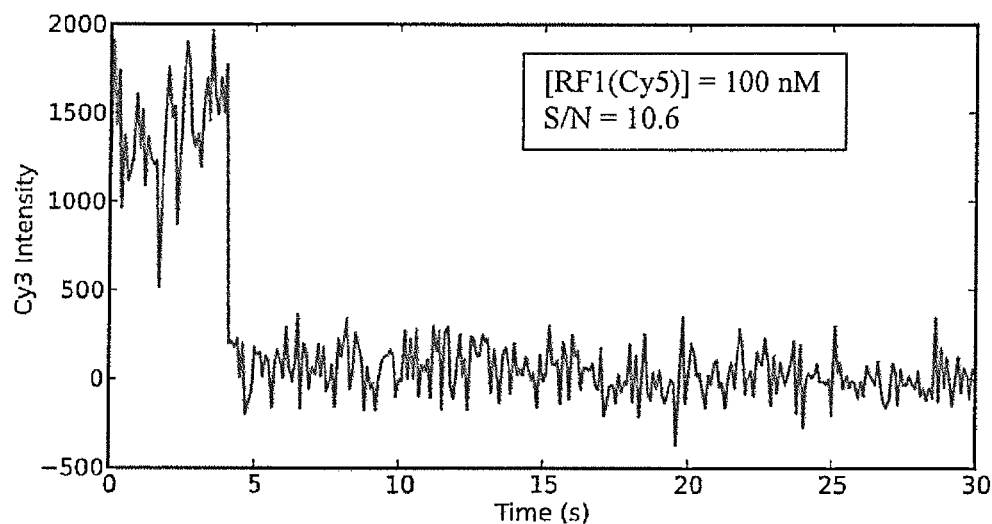
Figure 10D:
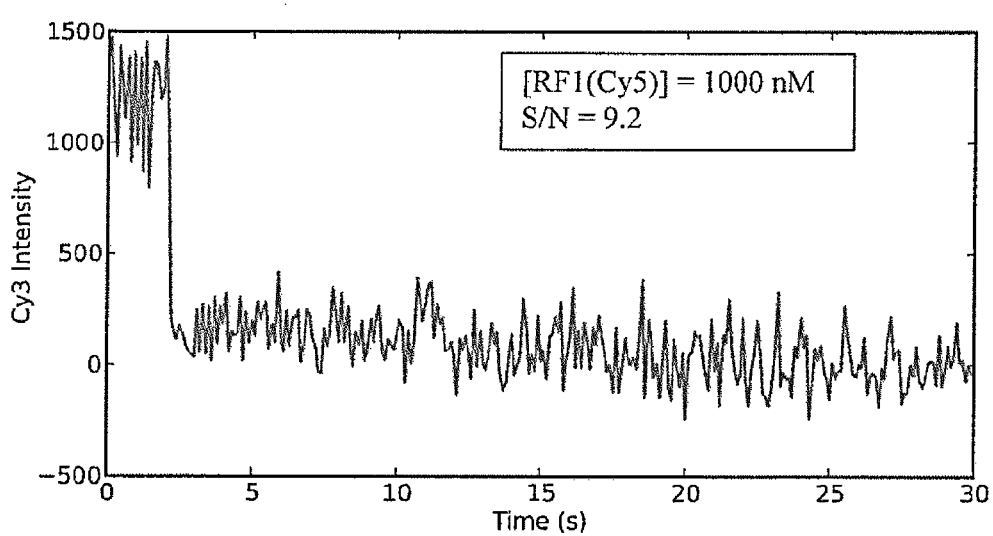

By correlating the number of individual Cy3 photobleach-ing events observed in the Cy3 fluorescence intensity versus time trajectories to the Cy3 fluorescence intensity observed per nanoaperture, the absolute number of Cy3- and Cy5-labeled bio-RF1$_{S167C,E256C}$ molecules that corresponded to each peak in the histogram was determined. The peaks in the histogram of FIGS. 9A, 9B and 9C correspond to nanoap-ertures that contain either one, two or three biotin-strepta-vidin-biotin-tethered, fluorescing Cy3- and Cy5-labeled bio-RF1$_{S167C,E256C}$ molecules, respectively (see also FIG. 12, insets). As expected, doubling the biotin-PEG-Si: PEG-Si ratio from 1:600 to 1:300 increases the populations of Cy3 fluorescence intensities corresponding to higher numbers of Cy3- and Cy5-labeled bio-RF1$_{S167C,E256C}$ molecules per nanoaperture. In addition, control over the distribution of Cy3- and Cy5-labeled bio-RF1$_{S167C,E256C}$ molecules per nanoaperture can be achieved by altering the concentrations and incubation times of streptavidin and Cy3- and Cy5-labeled bio-RF1$_{S167C,E256C}$. For the nanoaperture arrays of the dimensions used here, in certain embodiments, a 1:1000 ratio of biotin-PEG-Si:mPEG-Si with a 5 minute incubation at room temperature in 1 µM streptavidin followed by a 5 minute incubation at room temperature in 10-100 pM Cy3- and Cy5-labeled bio-RF1$_{S167C,E256C}$ was found to yield a maximal population of nanoapertures that contain a single Cy3- and Cy5-labeled bio-RF1$_{S167C,E256C}$ molecule.

Taken together with the streptavidin dependence shown in FIG. 8, the ability to predictably control the distribution of Cy3- and Cy5-labeled bio-RF1$_{S167C,E256C}$ molecules per nanoaperture by altering the ratio of biotin-PEG-Si:mPEG-Si demonstrates that the tethering of Cy3- and Cy5-labeled bio-RF1$_{S167C,E256C}$ molecules to the silica nanoaperture bottoms is specifically dependent on the presence of a biotin-streptavidin-biotin bridge. Moreover, the chemistries employed are general enough to produce similar results in different nanoaperture geometries (e.g., squares) and with side walls made of other metals that can form thiol SAMs (e.g., silver).

Example 6—FRET of RF1$_{S167C,E256C}$

High background concentrations of ligand biomolecules and/or the non-specific adsorption of ligand biomolecules can cause deterioration of the signal-to-background ratio (SBR) (also referred to herein as signal-to-noise ratios (S/N)) in FRET-based smF experiments used to characterize weak biomolecular interactions. This is a limitation of FRET-based smF experiments that can be overcome with the passivated, gold-based nanoapertures described herein. In this Example, experiments were performed to simulate the conditions of a FRET-based smF experiment without the usual complications to the FRET efficiency versus time trajectories that are introduced by the binding and dissociation of FRET acceptor-labeled ligand biomolecules from solution to individual, surface-tethered, FRET donor labeled target biomolecules.

As shown in FIGS. 10A-10D, signal-to-noise (S/N) ratio of the fluorescence signal of a single-molecule within a passivated nanoaperture (both the gold surface and the silica surface) does not decrease significantly with the titration of fluorophore-labeled protein, Cy5-labeled RF1$_{S167C}$ (RF1 (Cy5)), into the nanoapertures over a range that includes 0, 1, 10, 100 and 1000 nanomolar concentrations of this protein. Reaching 1000 nanomolar concentrations of background, fluorophore-labeled protein can allow many systems to be investigated with the disclosed nanoapertures by fluorescence microscopies at physiologically-relevant concentrations of fluorophore-labeled biomolecules.

Figure 13A:
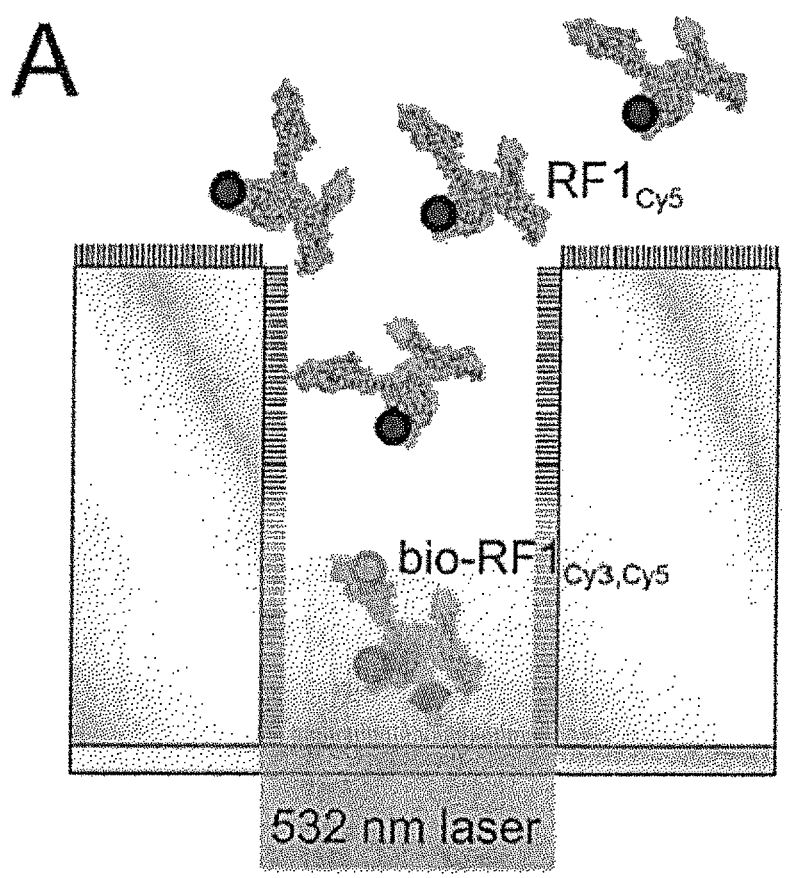
FIG. 13A shows a schematic diagram of a nanoaperture fluorescence microscopy experiment designed to simulate the effect of increasing background concentrations of a FRET acceptor labeled ligand biomolecule on a FRET-based nanoaperture fluorescence microscopy experiment.

In addition, the FRET-based titration experiment diagramed in FIG. 13A was performed. Briefly, a biotin-streptavidin-biotin bridge was used to specifically tether Cy3- and Cy5-labeled bio-RF1$_{S167C,E256C}$ molecules to the silica nanoaperture bottoms of a fully passivated (1:1000 biotin-PEG-Si:mPEG-Si) nanoaperture array and imaged a single flow cell at successively higher background solution concentrations of a Cy5 FRET acceptor-labeled variant of RF1 (Cy5-labeled RF1$_{S167C}$). To observe FRET signals arising from individual Cy3- and Cy5-labeled bio-RF1$_{S167C,E256C}$ molecules tethered to the silica nanoapertures bottoms, the Cy3 and Cy5 fluorescence intensities from individual, single Cy3- and Cy5-labeled bio-RF1$_{S167C,E256C}$ occupancy nanoapertures ($I_{Cy3}$ and $I_{Cy5}$, respectively) were converted into FRET efficiency, $E_{FRET}=I_{Cy5}/(I_{Cy3}+I_{Cy5})$, which is a ratiometric measure of acceptor-fluorophore fluorescence.

Figure 11A:
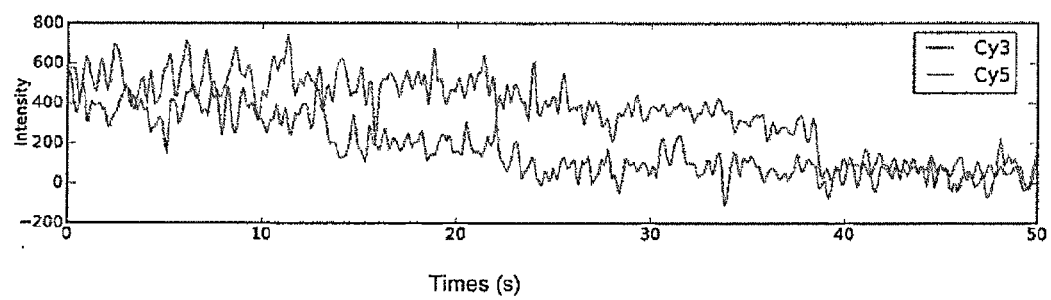
FIG. 11A is the fluorescence intensity time traces of FRETing a single Cy3- and Cy5-labeled bio-RF1$_{S192C,E256C}$ molecule in a nanoaperature according to the disclosed subject matter.
Figure 11B:
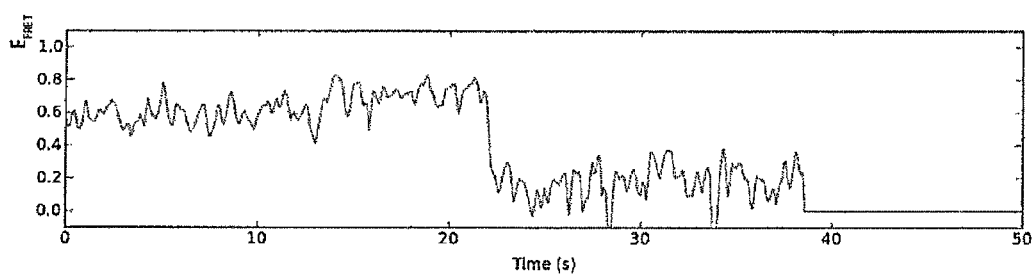
FIG. 11B is the $E_{FRET}$ versus time trace of the Cy3- and Cy5-labeled bio-RF1$_{S167C,E256C}$ molecule shown in FIG. 11A.

Although FRET signals arising from nanoapertures containing single Cy3- and Cy5-labeled bio-RF1$_{S167C,E256C}$ molecules were observed, the resulting $E_{FRET}$ versus time trajectories were characterized by a very low SBR (FIGS. 11A and B). This reduction in the SBR of $E_{FRET}$ versus time trajectories can be caused by quenching of Cy3 and/or Cy5 that arises from close proximity of these fluorophores to the gold surface, by a red-shift of the fluorescence emission of Cy5 past the filter bandwidth, or that the Cy3- and Cy5-labeled bio-RF1$_{S167C,E256C}$ construct exists mostly in a conformation where Cy3 and Cy5 are too far away from each other so as to undergo appreciable energy transfer is an unlikely explanation, given that energy transfer between Cy3 and Cy5 in TIRF-based FRET experiments was observed using this same Cy3- and Cy5-labeled bio-RF1$_{S167C,E256C}$.

Figure 13B:
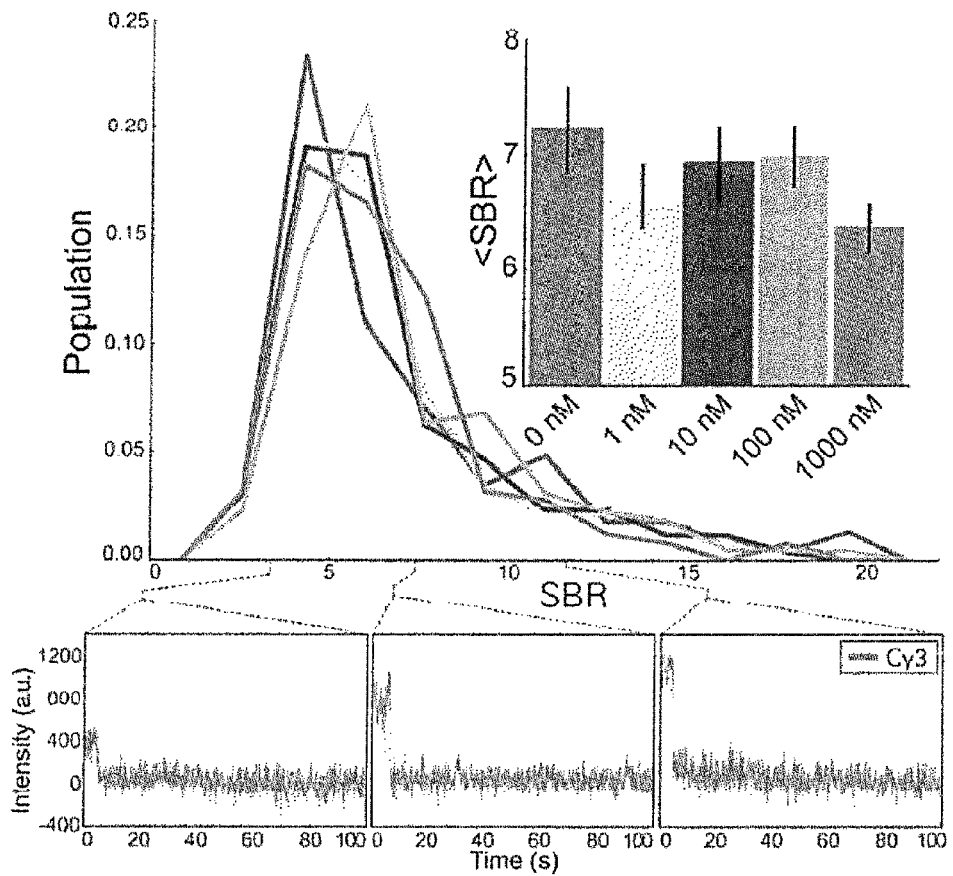
FIG. 13B shows distributions of Cy3 signal-to-background ratios (SBRs; calculated as the change in Cy3 fluorescence intensity due to photobleaching divided by the standard deviation of pure background fluorescence) imaged with 0 nM (n=136), 1 nM (n=137), 10 nM (n=155), 100 nM (n=131), and 1000 nM (n=146) background concentrations of bio-RF1$_{S167C}$. Representative Cy3 fluorescence intensity versus time trajectories at specific SBRs from the 1000 nM bio-RF1$_{S167C}$ data set are shown. The inset shows the average SBRs with bootstrapped, 1σ error bars (n=1000).

In order to quantify the ability of the nanoapertures to resist the SBR deterioration caused by high ligand biomolecule concentrations in solution and/or non-specific adsorption of ligand biomolecules to the nanoaperture surfaces, the SBR distributions of Cy3 fluorescence intensity observed during this experiment was calculated. As a reference, the SBR of the analogous TIRF microscopy experiment drops prohibitively low with greater than about 0 nM of Cy5-labeled RF1$_{S167C}$ in solution. After nonlinear least squares fitting a step function to each Cy3 fluorescence intensity versus time trajectory observed in single Cy3- and Cy5-labeled bio-RF1$_{S167C,E256C}$ occupancy nanoapertures, the SBR was calculated as the Cy3 fluorescence intensity difference due to photobleaching divided by the standard deviation of pure background fluorescence (measured using the last 50 photobleached timepoints of each Cy3 fluorescence intensity versus time trajectory), and the SBR distribution of approximately 130-150 single Cy3- and Cy5-labeled bio-RF1$_{S167C,E256C}$ molecules was plotted per background concentration of Cy5-labeled RF1$_{S167C}$ that was tested (FIG. 13B). An insignificant decrease in the average SBR was observed at the highest background concentration of Cy5-labeled RF1$_{S167C}$ tested (1 µM). In certain embodiments, the fully passivated, gold nanoaperture arrays reported herein can continue to enable detection of single Cy3- and Cy5-labeled bio-RF1$_{S167C,E256C}$ molecules with adequate SBR at concentrations of Cy5-labeled RF1$_{S167C}$ much greater than 1 µM.

Figure 17:
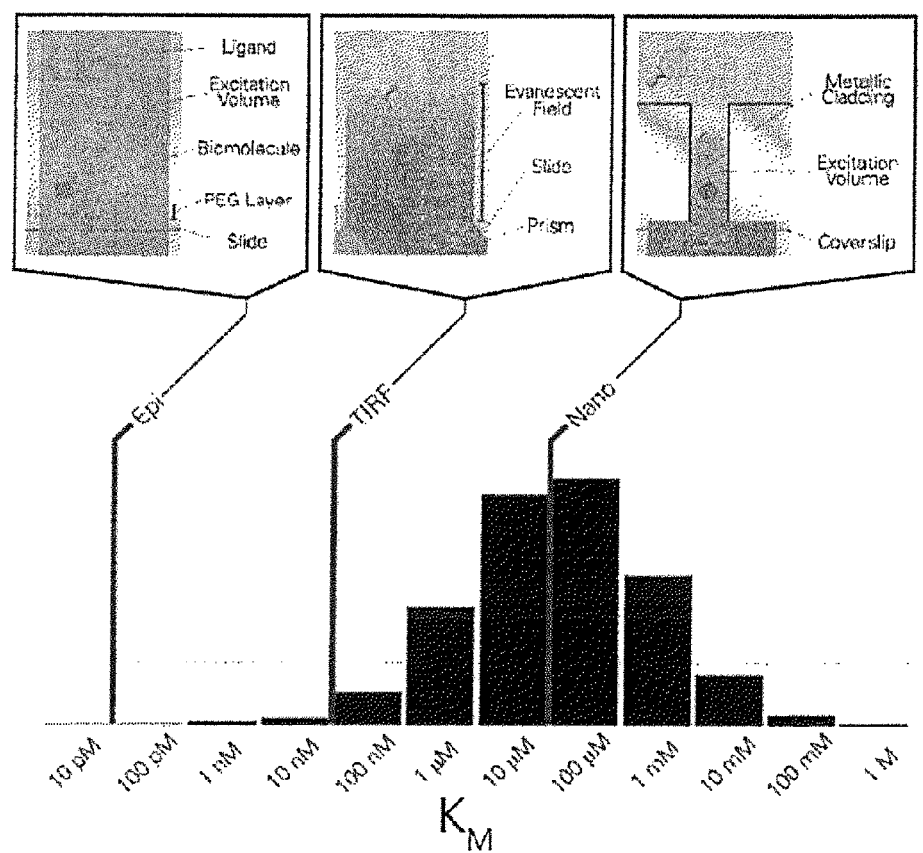
FIG. 17 shows a diagram of concentration ranges accessible by various microscopy techniques.

While nanoaperture fluorescence microscopy is an optical confinement-based microscopy that permits smF measurements to be made at physiologically-relevant, background concentrations of ligand biomolecules (FIG. 17), the non-specific adsorption of these ligand biomolecules to the metallic and silica nanoaperture surfaces often compromises the signal-to-background ratio (SBR) of the smF data. The bold lines of FIG. 17 represent the upper limit of the background concentration of ligand biomolecules that can be employed in smF experiments using epi-fluorescence microscopy (Epi), TIRF microscopy (TIRF), and nanoaperture fluorescence microscopy (Nano). The microscope schematics connected to each provide line provide molecular-level diagrams corresponding to each technique (upper panel). The histogram shows the distribution of Michaelis constants ($K_M$), a characterization of the interactions between enzymes and their corresponding substrates, of all eukaryotic enzymes in the BRENDA enzyme database (FIG. 17). This distribution is analogous to the distribution of background concentrations of ligand biomolecules required to observe interactions with a target biomolecule on an experimentally accessible timescale using smF microscopies (lower panel).

In order to overcome this problem, an orthogonal surface chemistry process was developed to selectively passivate the metallic cladding and silica bottoms of nanoapertures. Unfortunately, this process is quite limited, as it uses negatively charged poly(vinyl) phosphonic acid (PVPA) to minimize the non-specific adsorption of negatively charged, fluorophore-labeled deoxynucleotides for single molecule DNA sequencing applications, and it is not generally applicable to other biomolecular systems. The lack of significant progress in the development of more generalizable surface passivation chemistries has thus far restricted the use of nanoaperture fluorescence microscopy to only a handful of biological systems over the decade since nanoaperture fluorescence microscopy of biological systems was first introduced.

The passivated nanoaperture arrays described herein can be used to probe biological interactions under physiological concentrations of ligand biomolecules with a protein of interest, RF1. Notably, straightforward extensions of these experiments enable the structural dynamics of RF1 to be characterized as it weakly interacts with ribosomes programmed with non-stop messenger RNA codons—previously impracticable smF experiments that will allow us to investigate the mechanisms governing the fidelity with which RF1 recognizes stop codons and terminates protein synthesis. Moreover, the robust nature of the non-specific adsorption-resistance of PEG SAMs shows that the passivation scheme presented herein can be resistant to the non-specific adsorption of many other types of biomolecules. Furthermore, the plasmon-mediated fluorescence enhancements that are attainable with a variety of gold nanoaperture geometries are fully compatible with the surface functionalization approaches presented herein, a benefit that can be exploited in future developments of the nanoaperture array design reported herein.

Example 7—Microfluidic Device Fabrication

The significant SBR deterioration caused by the non-specific adsorption of ligand biomolecules onto the metallic and silica surfaces of nanoaperture arrays, as well as difficulties in the nanofabrication, passivation and microscopy of nanoaperture arrays, have been major limiting factors for the widespread adoption of nanoaperture fluorescence microscopy for smF studies of biological systems. By combining a facile, cost-effective and widely accessible procedure for fabricating and functionalizing gold nanoaperture arrays as disclosed herein, a microfluidic device can be generated that can enable powerful new smF experiments of weakly interacting biological systems that were previously impracticable with microscopy techniques such as TIRF.

Figure 14:
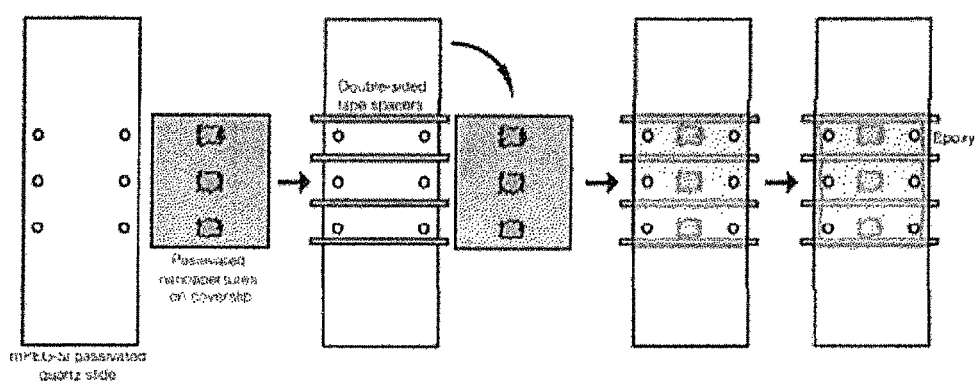
FIG. 14 shows a schematic of a microfluidic device of an exemplary embodiment of the disclosed subject matter.

The nanoaperture arrays disclosed herein were further used to fabricate a microfluidic device (FIG. 14). A quartz microscope slide was drilled to form sets of inlet/outlet ports and cleaned using a previously published procedure (Ha, T et al., Nature, 419:638-41 (2002), and passivated with mPEG-Si. Thin, adhesive spacers were carefully placed between the inlet/outlet ports of an mPEG-Si passivated, quartz microscope slide. The borosilicate coverslip substrate containing the passivated nanoaperture arrays, as disclosed herein, were placed on the adhesive spacers, and aligned such that the nanoaperture arrays were positioned between the spacers, facing the interior of the soon-to-be flow cells. This alignment was facilitated by placing the slide on an illuminated surface, and then using the diffraction from the nanoaperture arrays as a guide. Once the coverslip was affixed to the slide, the flow cells were sealed with fast-drying epoxy. The superfluous spacer and epoxy can be removed from the sides of the microfluidic device with a razor blade once the epoxy was cured. This multiple flow cell geometry allowed for several independent experiments and controls to be performed in the same microfluidic device, thereby eliminating device fabrication and processing as a source of experimental variation.

Example 8—Comparison Analysis

Figure 15A:
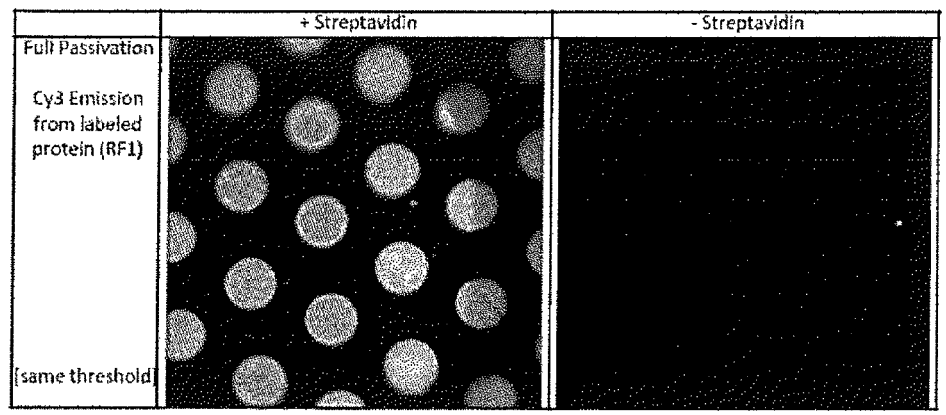
FIGS. 15A and 15B are fluorescence images of macro-sized wells with exposed silica bottom surface and gold side walls at different test and passivation conditions.
Figure 15B:
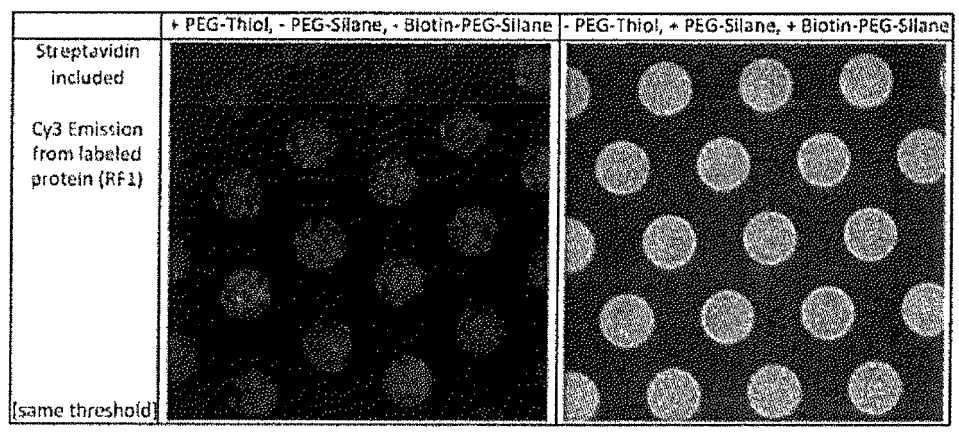

A glass slide was coated with a 100 nm thick gold, and a plurality of circular, micro-sized wells of 5 µm in diameter were made on the gold layer to expose the silica surface. RF1 labeled with Cy3 and Cy5 was used as the test biomolecule. For the results shown in FIG. 15A, a thiol-PEG molecule was used to passivate the gold surface, and then a dilute solution of biotin-PEG-Si (in its mixture with mPEG-Si) was used to passivate the exposed silica areas. As shown in FIG. 15A, when streptavidin was used (left image), the fluorescence signals of the RF1 were prominent (Cy3 emission, as indicated by the bright circular areas). As a control test, FIG. 15B shows that when the gold was not passivated whereas the silica was passivated by silane-PEG/biotin-PEG-Si, the fluorescence of RF1 was diminished by only a few percent. This can be explained by the fact that streptavidin absorbs on bare gold more than RF1. In contrast, when only the gold surface was passivated by thiol-PEG and the silica surface was not passivated, the Cy3 emission of the RF1 was significantly reduced.

While the disclosed subject matter is described herein in terms of certain embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A zero-mode waveguide, comprising:
(a) a substrate; and
(b) a sub-wavelength nanoaperture on the substrate, the nanoaperture having a bottom surface and a side wall, wherein the side wall comprises gold,
wherein a surface of the side wall is passivated with at least one first functional molecule comprising polyethylene glycol,
wherein the at least one first functional molecule is attached to the surface of the side wall via a S—Au linkage,
wherein the nanoaperture has a cross dimension less than a wavelength of incident light used for the nanoaperture divided by 1.7 and the wavelength of incident light is between about 10 nm to about 2000 nm, and wherein the bottom surface of the nanoaperture is functionalized with at least one second molecule comprising a mixture of (1) at least one molecule comprising polyethylene glycol and a moiety adapted for binding with a target biomolecule, and (2) at least one molecule comprising polyethylene glycol and no moiety adapted for binding with the target biomolecule.

2. The zero-mode waveguide of claim 1, wherein the nanoaperture has a width of from about 25 to about 500 nm.

3. The zero-mode waveguide of claim 1, wherein the side wall has a height of from about 50 to about 500 nm.

4. The zero-mode waveguide of claim 1, wherein the at least one first functional molecule form a monolayer on the surface of the side wall.

5. The zero-mode waveguide of claim 1, wherein the polyethylene glycol of the first functional molecule comprises from about 1 to about 200 ethylene oxide units.

6. The zero-mode waveguide of claim 1, wherein the polyethylene glycol of the second functional molecule comprises from about 1 to about 200 ethylene oxide units.

7. The zero-mode waveguide of claim 1, wherein the moiety comprises a biotin moiety.

8. The zero-mode waveguide of claim 1, wherein the target biomolecule comprises streptavidin.

9. The zero-mode waveguide of claim 1, wherein the bottom surface comprises silica, and the at least one second molecule further comprises a silane group and is attached to the bottom surface via a Si—O—Si linkage.

10. The zero-mode waveguide of claim 1, further comprising a layer of a metal selected from the group consisting of titanium, chromium and a combination thereof disposed between the substrate and the side wall of the at least one nano-well.

11. The zero-mode waveguide of claim 1, wherein the substrate comprises silica.

12. A method for fabricating a zero-mode waveguide, comprising:
 (a) forming a sub-wavelength nanoaperture on a substrate, the nanoaperture having a bottom surface and a side wall, wherein the side wall comprises gold;
 (b) passivating a surface of the side wall with at least one first functional molecule comprising polyethylene glycol, wherein the at least one first functional molecule comprises a thiol group, and wherein the passivating comprises reacting the thiol group with the surface of the side wall to form a S—Au bond coupling the first functional molecule with the surface of the side wall, and
 wherein the nanoaperture has a cross dimension less than a wavelength of incident light used for the nanoaperture divided by 1.7 and the wavelength of incident light is between about 10 nm to about 2000 nm; and
 (c) functionalizing the bottom surface of the nanoaperture with at least one second molecule comprising a mixture of (1) at least one molecule comprising polyethylene glycol and having a moiety adapted for binding with a target biomolecule, and (2) at least one molecule comprising polyethylene glycol and having no moiety adapted for binding with the target biomolecule.

13. The method of claim 12, wherein the at least one second functional molecule comprises a silane group, wherein the bottom surface of the nanoaperture comprises silica, and wherein the functionalizing comprises reacting the silane group with the bottom surface to form a Si—O—Si bond coupling the second functional molecule with the bottom surface.

14. The method of claim 12, wherein the moiety comprises a biotin moiety, and the target biomolecule comprises streptavidin.

15. The method of claim 12, wherein the substrate is a silica substrate, and wherein the forming of the nanoaperture further comprises:
 (a) applying a photoresist on the surface of the silica substrate;
 (b) forming one nano-column in the photoresist by etching;
 (c) depositing a thin layer of titanium on the substrate;
 (d) depositing a layer of gold onto the layer of titanium; and
 (e) removing the nano-column in the photoresist, thereby creating the nanoaperture having a bottom surface and a side wall comprising gold.

16. A nanoaperture array, comprising:
 (a) a substrate; and
 (b) two or more nanoapertures on the substrate, where each nanoaperture of the two or more nanoapertures has a bottom surface and a side wall,
 wherein the side wall comprises gold,
 wherein a surface of the side wall is passivated with at least one first functional molecule comprising polyethylene glycol,
 wherein the at least one first functional molecule is attached to the surface of the side wall via a S—Au bond,
 wherein the nanoaperture has a cross dimension less than a wavelength of incident light used for the nanoaperture divided by 1.7 and the wavelength of incident light is between about 10 nm to about 2000 nm, and
 wherein the bottom surfaces of the two or more nanoapertures are functionalized with at least one second functional molecule comprising a mixture of (1) at least one molecule comprising polyethylene glycol and a moiety adapted for binding with a target biomolecule, and (2) at least one molecule comprising polyethylene glycol and no moiety adapted for binding with the target biomolecule.

17. The nanoaperture array of claim 16, wherein each nanoaperture of the two or more nanoapertures has a width of from about 25 to about 500 nm.

18. The nanoaperture array of claim 16, wherein the side wall has a height of from about 50 to about 500 nm.

19. The nanoaperture array of claim 16, wherein each nanoaperture of the two or more nanoapertures is spaced from about 500 nm to about 5 μm to each other.

20. The nanoaperture array of claim 16, wherein the at least one first functional molecule form a monolayer on the surface of the side wall.

21. The nanoaperture array of claim 16, wherein the polyethylene glycol of the first functional molecule comprises from about 1 to about 200 ethylene oxide units.

22. The nanoaperture array of claim 16, wherein the polyethylene glycol of the second functional molecule comprises from about 1 to about 200 ethylene oxide units.

23. The nanoaperture array of claim 16, wherein the moiety comprises a biotin moiety.

24. The nanoaperture array of claim 16, wherein the target biomolecule is streptavidin.

25. The nanoaperture array of claim 16, wherein the bottom surfaces comprise silica, and the at least one second molecule comprises a silane group and is attached to the bottom surfaces via a Si—O—Si linkage.

26. The nanoaperture array of claim 16, further comprising a layer of a metal selected from the group consisting of titanium, chromium and a combination thereof between the substrate and the side wall of each nanoaperture of the two or more nanoapertures.

27. The nanoaperture array of claim 16, wherein the substrate comprises silica.

28. The nanoaperture array of claim 16, wherein the at least one molecule comprising polyethylene glycol and a moiety adapted for binding with a target biomolecule and the at least one molecule comprising polyethylene glycol and no moiety adapted for binding with the target biomolecule are present in the mixture at a ratio of about 1:100 to about 1:10,000.

29. A method for fabricating a nanoaperture array, comprising:
   (a) forming two or more nanoapertures on a substrate, each nanoaperture of the two or more nanoapertures has a bottom surface and a side wall, wherein the side wall comprises gold;
   (b) passivating a surface of the side wall with at least one first functional molecule comprising polyethylene glycol, wherein the at least one first functional molecule comprises a thiol group, and wherein the passivating comprises reacting the thiol group with the surface of the side wall to form a S—Au bond coupling the first functional molecule with the surface of the side wall, wherein the nanoaperture has a cross dimension less than a wavelength of incident light used for the nanoaperture divided by 1.7 and the wavelength of incident light is between about 10 nm to about 2000 nm; and
   (c) functionalizing the bottom surfaces of the two or more nanoapertures with at least one second functional molecule comprising a mixture of (1) at least one molecule comprising polyethylene glycol and having a moiety adapted for binding with a target biomolecule, and (2) at least one molecule comprising polyethylene glycol and having no moiety adapted for binding with the target biomolecule.

30. The method of claim 29, wherein the at least one second functional molecule comprises a silane group, wherein the bottom surfaces of the two or more nanoapertures comprise silica, and wherein the functionalizing comprises reacting the silane end group with the bottom surface to form a Si—O—Si bond coupling the second functional molecule with the bottom surface.

31. The method of claim 29, wherein the moiety comprises a biotin moiety, and the target biomolecule is streptavidin.

32. The method of claim 29, wherein the substrate is a silica substrate, wherein the forming two or more nanoapertures further comprises:
   (a) applying a photoresist on the surface of the silica substrate;
   (b) forming two or more cylindrical columns in the photoresist by etching;
   (c) depositing a thin layer of titanium on the substrate;
   (d) depositing a layer of gold onto the layer of titanium; and
   (e) removing two or more cylindrical columns in the photoresist, thereby creating the two or more nanoapertures having a bottom surface and a side wall comprising gold.

33. A microfluidic device, comprising:
(a) a support material;
(b) one or more nanoaperture arrays on the support, wherein the one or more nanoaperture arrays comprises:
   (i) a substrate; and
   (ii) two or more nanoapertures on the substrate, each nanoaperture of the two or more nanoapertures has a bottom surface and a side wall,
      wherein the side wall comprises gold,
      wherein a surface of the side wall is passivated with at least one first functional molecule comprising polyethylene glycol, and
      wherein the at least one first functional molecule is attached to the surface of the side wall via a S—Au linkage;
   wherein the nanoaperture has a cross dimension less than a wavelength of incident light used for the nanoaperture divided by 1.7 and the wavelength of incident light is between about 10 nm to about 2000 nm, and
      wherein the bottom surfaces of the two or more nanoapertures are functionalized with at least one second functional molecule comprising a mixture of (1) at least one molecule comprising polyethylene glycol and a moiety adapted for binding with a target biomolecule, and (2) at least one molecule comprising polyethylene glycol and no moiety adapted for binding with the target biomolecule;
(c) one or more inlet ports coupled to the one or more nanoaperture arrays; and
(d) one or more outlet ports coupled to the one or more nanoaperture arrays.

34. A zero-mode waveguide, comprising:
(a) a substrate; and
(b) a sub-wavelength nanoaperture on the substrate, the nanoaperture having a bottom surface and a side wall, wherein the side wall comprises gold,
   wherein a surface of the side wall is passivated with at least one first functional molecule comprising polyethylene glycol,
   wherein the at least one first functional molecule is attached to the surface of the side wall via a S—Au linkage,
   wherein the nanoaperture confines a wavelength of incident light to an about 0 nm to 50 nm bottom region of the nanoaperture and the height of the side wall is greater than 50 nm, and
   wherein the bottom surface of the nanoaperture is functionalized with at least one second molecule comprising a mixture of (1) at least one molecule comprising polyethylene glycol and a moiety adapted for binding with a target biomolecule, and (2) at least one molecule comprising polyethylene glycol and no moiety adapted for binding with the target biomolecule.

* * * * *